United States Patent [19]
Sohda et al.

[11] Patent Number: 5,965,589
[45] Date of Patent: *Oct. 12, 1999

[54] THIAZOLIDINEDIONE DERIVATIVES, THEIR PRODUCTION AND USE

[75] Inventors: Takashi Sohda, Takatsuki; Hiroyuki Odaka, Kobe; Yu Momose, Takarazuka, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/530,115

[22] PCT Filed: Aug. 9, 1995

[86] PCT No.: PCT/JP95/01579

§ 371 Date: Oct. 5, 1995

§ 102(e) Date: Oct. 5, 1995

[87] PCT Pub. No.: WO96/05186

PCT Pub. Date: Feb. 22, 1996

[30] Foreign Application Priority Data

Aug. 10, 1994 [JP] Japan ..................... 6/188611

[51] Int. Cl.[6] ................. C07D 413/12; A61K 31/42
[52] U.S. Cl. ........................... 514/369; 548/183
[58] Field of Search ............... 548/183; 514/369

[56] References Cited

U.S. PATENT DOCUMENTS

| | | | |
|---|---|---|---|
| 4,725,610 | 2/1988 | Meguro et al. | 514/369 |
| 5,063,240 | 11/1991 | Hindley | 514/369 |
| 5,130,379 | 7/1992 | Clark et al., II | 514/333 |
| 5,330,998 | 7/1994 | Clark et al., I | 514/369 |
| 5,468,762 | 11/1995 | Malamas et al., II | 514/376 |
| 5,478,852 | 12/1995 | Olefsky et al. | 514/369 |
| 5,532,256 | 7/1996 | Malamas et al., I | 514/361 |

FOREIGN PATENT DOCUMENTS

| | | |
|---|---|---|
| 0 332 331 | 9/1989 | European Pat. Off. . |
| 0 332 332 | 9/1989 | European Pat. Off. . |
| 0508740A1 | 10/1992 | European Pat. Off. . |
| 0 604 983 A1 | 7/1994 | European Pat. Off. . |
| 0 605 228 A1 | 7/1994 | European Pat. Off. . |
| 4-66579 | 3/1992 | Japan . |
| 4-69383 | 3/1992 | Japan . |

*Primary Examiner*—Patricia L. Morris
*Attorney, Agent, or Firm*—Wenderoth, Lind & Ponack, L.L.P.

[57] ABSTRACT

A 2,4-thiazolidinedione derivative of the formula (I):

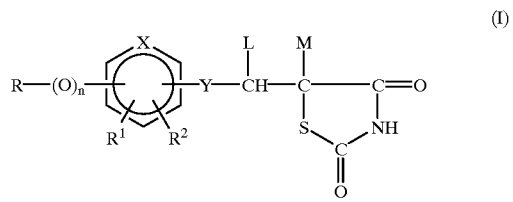

wherein R is an optionally substituted hydrocarbon group or heterocyclic group which may be attached through a hydrocarbon chain; n is 0 or 1; X is CH or N; Y is a bivalent hydrocarbon group; $R^1$ and $R^2$ are the same or different and are a hydrogen atom, a halogen atom, an optionally substituted hydroxyl group or an optionally substituted hydrocarbon group, and either $R^1$ or $R^2$ and a part of Y may be linked together to form a ring; and L and M are a hydrogen atom, or L and M are linked together to form a bond; or a salt thereof. A pharmaceutical composition comprising the compound (I) and a process for producing the compound (I) are also provided.

12 Claims, No Drawings

THIAZOLIDINEDIONE DERIVATIVES, THEIR PRODUCTION AND USE

TECHNICAL FIELD

The present invention relates to a novel thiazolidinedione derivative having hypoglycemic activity and blood lipid lowering activity, production thereof, and an antidiabetic agent containing it. The present invention is useful in the field of medicine.

BACKGROUND OF ART

As an agent for treating diabetes, various biguanide compounds and sulfonylurea compounds have been used. However, biguanide compounds are now hardly used because of their side effect of lactic acid acidosis. Although sulfonylurea compounds have potent hypoglycemic activity, they often cause serious hypoglycemia and must be used with care.

Thiazolidinedione derivatives having hypoglycemic activity and blood lipid lowering activity without the above disadvantages have been known. For example, JP-A 61-85372, JP-A 1-272573, JP-A 1-272574, JP-A 3-2173, JP-A 4-66579, JP-A 4-69383, JP-A 6-157522, etc., disclose 2,4-thiazolidinedione derivatives having at the 5-position a substituent such as a benzyl group or an arylmethyl group substituted by a substituted aromatic ring, etc.

DISCLOSURE OF INVENTION

The present inventors have intensively studied 2,4-thiazolidinedione derivatives. As a result, it has been found that a novel 2,4-thiazolidinedione derivative has hypoglycemic activity and blood lipid lowering activity, said 2,4-thiazolidinedione derivative having at the 5-position a substituent such as a 2-(substituted phenyl or substituted pyridyl)ethyl group, a 3-(substituted phenyl or substituted pyridyl)propyl group, a 4-(substituted phenyl or substituted pyridyl)butyl group, a 5-(substituted phenyl or substituted pyridyl)pentyl group, etc., and having a bivalent straight or branched hydrocarbon chain containing a substituted phenyl or substituted pyridyl group at the terminal (in the case of a branched hydrocarbon chain, a part of it and a substituent on the substituted phenyl group may be linked together to form a ring). Thus, the present invention has been completed.

The present invention provides a 2,4-thiazolidinedione derivative of the formula (I):

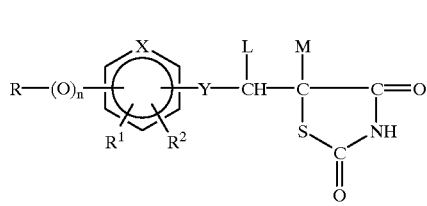

(I)

wherein
R is an optionally substituted hydrocarbon group or a heterocyclic group which may be attached through a hydrocarbon chain;
n is 0 or 1;
X is CH or N;
Y is a bivalent hydrocarbon group;
$R^1$ and $R^2$ are the same or different and are a hydrogen atom, a halogen atom, an optionally substituted hydroxyl group or an optionally substituted hydrocarbon group, and either $R^1$ or $R^2$ and a part of Y may be linked together to form a ring; provided that

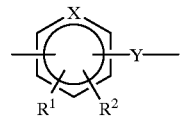

is other than

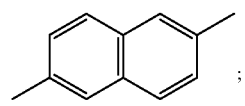

and
L and M are a hydrogen atom, or L and M are linked together to form a bond; or a salt thereof.

The present invention also provides a pharmaceutical composition which comprises a 2,4-thiazolidinedione derivative of the above formula (I) or a pharmaceutically acceptable salt thereof and a pharmaceutically acceptable carrier.

The present invention also provides a process for producing a 2,4-thiazolidinedione derivative of the formula (I-B2):

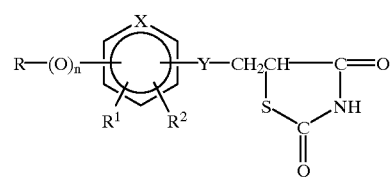

(I-B2)

wherein each symbol is as defined above, which comprises hydrolyzing an iminothiazolidinone compound of the formula (III):

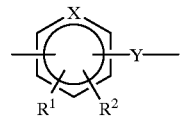

(III)

wherein each symbol is as defined above.

The present invention also provides a process for producing a 2,4-thiazolidinedione derivative of the formula (I-B2a):

(I-B2a)

wherein
R' is an optionally substituted hydrocarbon group or a heterocyclic group which may be attached through a saturated hydrocarbon chain;

$Y^1$ is a bivalent saturated hydrocarbon group;

either $R^1$ or $R^2$ and a part of $Y^1$ may be linked together to form a ring;

provided that

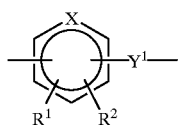

is other than

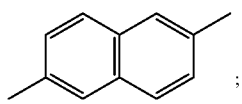

and the other symbols are as defined above; which comprises reducing a compound of the formula (I-B1):

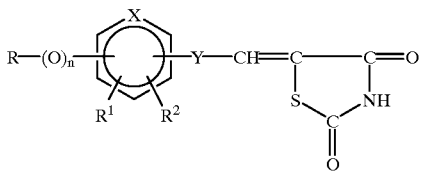

(I-B1)

wherein each symbol is as defined above.

The present invention also provides a process for producing a 2,4-thiazolidinedione derivative of the formula (I-D1):

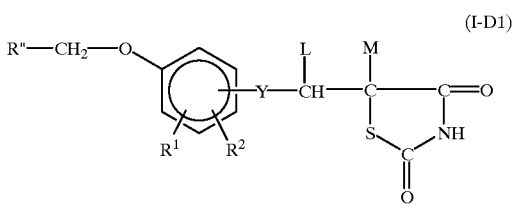

(I-D1)

wherein R" is a heterocyclic group and the other symbols are as defined above, which comprises reacting a compound of the formula (V):

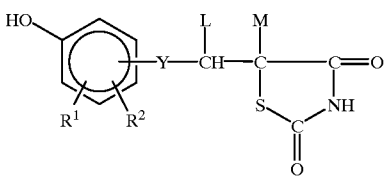

(V)

wherein each symbol is as defined above, with a compound of the formula (VI):

(VI)

wherein Q is a leaving group and R" is as defined above

The above compound of the formula (I) includes the compounds represented by the following formulas.

(I-A1)

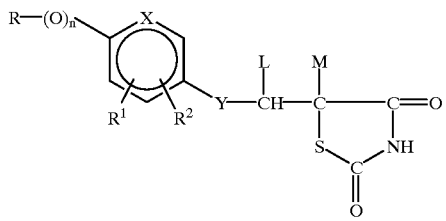

(I-A2)

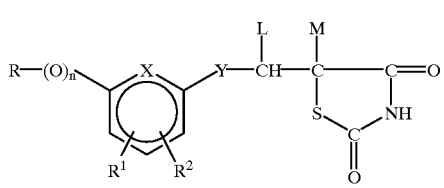

(I-A3)

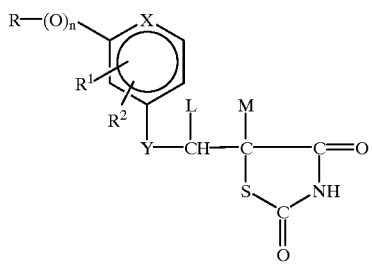

wherein each symbol is as defined above.

In view of the efficacy, toxicity, etc., of the compounds, the compounds of the formulas (I-A1) and (I-A2) are preferred among the compounds of the formulas (I-A1), (I-A2) and (I-A3). In particular, the compound of the formula (I-A1) is preferred.

When L and M in the formula (I) are linked together to form a bond, the compound of the formula (I) means a compound of the formula (I-B1):

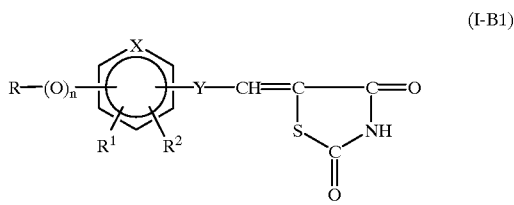

(I-B1)

wherein each symbol is as defined above. When L and M are each a hydrogen atom, the compound of the formula (I) means a compound of the formula (I-B2):

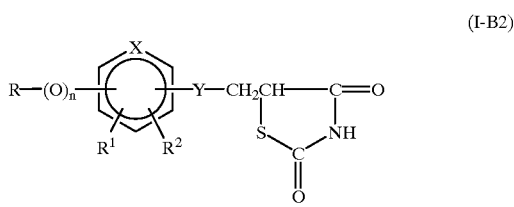

(I-B2)

wherein each symbol is as defined above.

The above compound of the formula (I-B1) has its (E)- and (Z)-isomers with respect to the double bond at the 5-position in the 2,4-thiazolidinedione ring.

The above compound of the formula (I-B2) has its (R)- and (S)-optically active substances with respect to the asymmetric carbon at the 5-position in the 2,4-thiazolidinedione ring, and includes these (R)- and (S)-optical isomers and racemic modifications.

Of the compounds of the formulas (I-B1) and (I-B2), the compound of the formula (I-B2) is preferred.

In the above formula (I), when any one or both of $R^1$ and $R^2$ are a hydrocarbon group, one of the hydrocarbon groups and a part of Y may be linked together to form a ring. Compounds in which $R^1$ and a part of Y are linked together to form a ring include the following compounds:

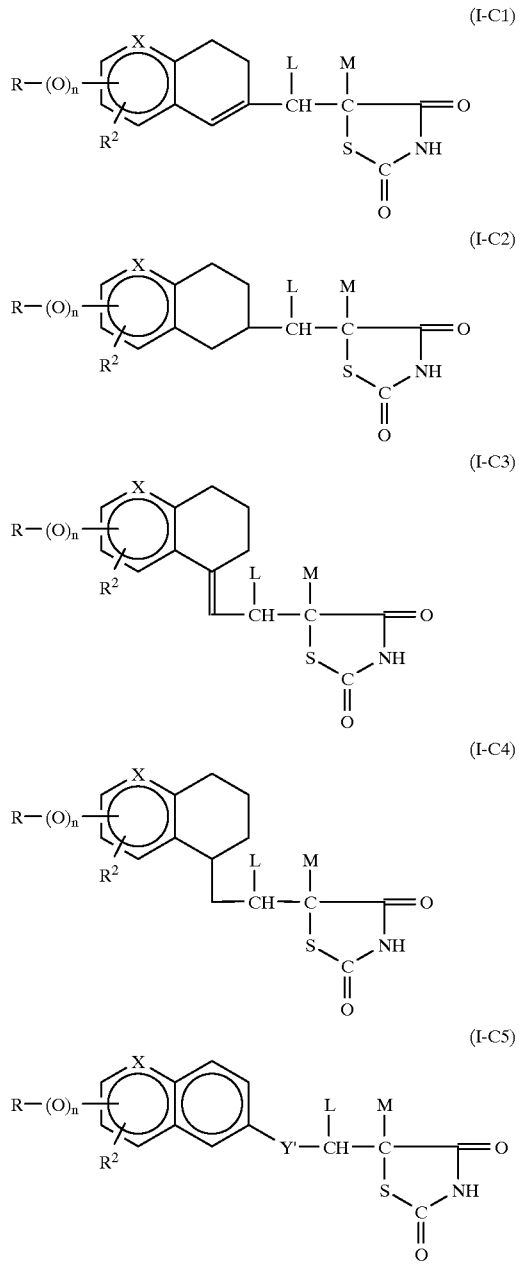

wherein Y' is a bivalent hydrocarbon group, and the other symbols are as defined above.

Of the above compounds of the formulas (I-C1) to (I-C4), the compounds of the formulas (I-C2) and (I-C4) are preferred.

In the heterocyclic group which may be attached through a hydrocarbon chain represented by R in the formula (I), the heterocyclic group is attached to $—(O)_n—$ directly or through a hydrocarbon chain. Preferably, it is attached through a hydrocarbon chain. The hydrocarbon chain may be straight or branched and saturated or unsaturated, and has preferably 1 to 8 carbon atoms. Examples of the hydrocarbon chain include the bivalent hydrocarbon groups represented by Y. Preferably, the hydrocarbon chain is a ethylene group ($—CH_2CH_2—$) or a vinylene group ($—CH=CH—$).

The heterocyclic group is preferably a 5- or 6-membered cyclic group or a condensed cyclic group, and has at least one ring-constituting nitrogen atom to form a nitrogen-containing heterocyclic group. Preferably, the heterocyclic group contains an aromatic ring having an unsaturated bond. The heterocyclic group may have not less than 2 ring-constituting nitrogen atoms, and may contain a heteroatom such as an oxygen atom or a sulfur atom in addition to a nitrogen atom.

Examples of the heterocyclic groups include pyrrolyl (e.g., 2-pyrrolyl), pyrazolyl (e.g., 3-pyrazolyl), imidazolyl (e.g., 2-imidazolyl, 4-imidazolyl), triazolyl (e.g., 1,2,3-triazol-4-yl, 1,2,4-triazol-3-yl), tetrazolyl, oxazolyl (e.g., 2-oxazolyl, 4-oxazolyl), thiazolyl (e.g., 2-thiazolyl, 4-thiazolyl), etc.

The heterocyclic group may have at least one substituent at any possible position on the ring. The substituents include hydrocarbon groups, heterocyclic groups and an amino group. These substituents may have further substituents.

The hydrocarbon groups as the substituent of the heterocyclic group in R include aliphatic hydrocarbon groups, alicyclic hydrocarbon groups, alicyclic-aliphatic hydrocarbon groups, (aromatic carbocycle)-aliphatic hydrocarbon groups, aromatic hydrocarbon groups, etc.

Examples of such aliphatic hydrocarbon groups include saturated aliphatic hydrocarbon groups (e.g., alkyl groups) having 1 to 8 carbon atoms, preferably 1 to 4 carbon atoms, such as methyl, ethyl, propyl, isopropyl, butyl, isobutyl, sec-butyl, t-butyl, pentyl, isopentyl, neopentyl, t-pentyl, hexyl, isohexyl, heptyl, octyl, etc.; unsaturated aliphatic hydrocarbon groups (e.g., alkenyl groups, alkynyl groups) having 2 to 8 carbon atoms, preferably 2 to 4 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl, etc.

Examples of such alicyclic hydrocarbon groups include saturated alicyclic hydrocarbon groups (e.g., cycloalkyl groups) having 3 to 7 carbon atoms, preferably 5 to 6 carbon atoms, such as cyclopropyl, cyclobutyl, cyclopentyl, cyclohexyl, cycloheptyl, etc.; and unsaturated alicyclic hydrocarbon groups (e.g., cycloalkenyl groups) having 5 to 7 carbon atoms, preferably 5 to 6 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.

Examples of such alicyclic-aliphatic hydrocarbon groups include those having 4 to 9 carbon atoms each of which is composed of the above alicyclic hydrocarbon group and aliphatic hydrocarbon group, such as cycloalkyl-alkyl groups, cycloalkenyl-alkyl groups, etc. Specific examples of the alicyclic-aliphatic hydrocarbon groups include cyclopropyl-methyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, etc.

Examples of such (aromatic carbocycle)-aliphatic hydrocarbon groups include phenylalkyl having 7 to 9 carbon atoms such as benzyl, phenethyl, 1-phenylethyl, 3-phenylpropyl, 2-phenylpropyl, 1-phenylpropyl, etc.; naphthyl-alkyl having 11 to 13 carbon atoms such as α-naphthylmethyl, α-naphtylethyl, β-naphthylmethyl, β-naphthylethyl, etc.

Examples of such aromatic hydrocarbon groups include phenyl, naphthyl (e.g., α-naphthyl, β-naphthyl), etc.

The heterocyclic group as the substituent of the heterocyclic group in R is a 5- or 6-membered cyclic group which contains 1 to 3 ring-constituting heteroatoms selected from a nitrogen atom, an oxygen atom and a sulfur atom in addition to a carbon atom and which is attached through a ring-constituting carbon atom. Examples thereof include unsaturated heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thazolyl, 4-thiazolyl, 5-thazolyl), oxazolyl (e.g., 2-oxazolyl, 4-oxazolyl, 5-oxazolyl), imidazolyl (e.g., 2-imidazolyl, 4-imidazolyl, 5-imidazolyl), pyrimidinyl (e.g., 2-pyrimidinyl, 4-pyrimidinyl, 5-pyrimidinyl, 6-pyrimidinyl), pyrazinyl, pyridazinyl (e.g., 3-pyridazinyl, 4-pyridazinyl, 5-pyridazinyl, 6-pyridazinyl), etc.; saturated heterocyclic groups such as piperidinyl (e.g., 2-piperidinyl, 3-piperidinyl, 4-piperidinyl), pyrrolidinyl (e.g., 2-pyrrolidinyl, 3-pyrrolidinyl), morpholinyl (e.g., 2-morpholinyl, 3-morpholinyl), tetrahydrofuryl (e.g., 2-tetrahydrofuryl, 3-tetrahydrofuryl), etc.

The amino group as the substituent of the heterocyclic group in R may be substituted. The substituted amino groups include N-monosubstituted amino groups and N,N-disubstituted amino groups.

Such N-monosubstituted amino group means an amino group having one substituent. Examples of the substituents include lower alkyl groups (e.g., alkyl groups having 1 to 4 carbon atoms such as methyl, ethyl, propyl, butyl, i-butyl, t-butyl, etc.), cycloalkyl groups (e.g., cycloalkyl groups having 3 to 7 carbon atoms such as cyclopentyl, cyclohexyl, etc.), aryl groups (e.g., phenyl, naphthyl, etc.), aromatic heterocyclic groups (e.g., pyridyl, thienyl, furyl, oxazolyl, thiazolyl, etc.), non-aromatic heterocyclic groups (e.g., piperidinyl, pyrrolidinyl, morpholinyl, etc.), aralkyl groups (e.g., benzyl, phenethyl, etc.), acyl groups (e.g., acetyl, propionyl, etc.), a carbamoyl group, N-monosubstituted carbamoyl groups (e.g., N-methylcarbamoyl, N-ethylcarbamoyl, N-propylcarbamoyl, etc.), N,N-disubstituted carbamoyl groups (e.g., N,N-dimethylcarbamoyl, N-methyl-N-ethylcarbamoyl, N,N-diethylcarbamoyl, etc.), lower alkoxycarbonyl groups (e.g., alkoxycarbonyl groups having 2 to 5 carbon atoms such as methoxycarbonyl, ethoxycarbonyl, propoxycarbonyl, etc.), a hydroxyl group, lower alkoxy groups (e.g., alkoxy groups having 1 to 4 carbon atoms such as methoxy, ethoxy, propoxy, butoxy, etc.), aralkyloxy groups (e.g., benzyloxy, phenethyloxy, naphthylmethyloxy, etc.), etc.

Such N,N-disubstituted amino group means an amino group having two substituents. One of the substituents is similar to the substituents of the above N-monosubstituted amino groups. Examples of the alkyl substituent include lower alkyl groups, cycloalkyl groups, aryl groups, aralkyl groups, etc. The two substituents may be linked together with the nitrogen atom to form a cyclic amino group.

Examples of the cyclic amino groups include 1-azetidinyl, pyrrolidino, piperidino, morpholino, piperazino, and piperazino having at the 4-position a lower alkyl group (e.g., alkyl having 1 to 4 carbon atoms such as methyl, ethyl, propyl, etc.), an aralkyl group (e.g., benzyl, phenethyl, naphthylmethyl, etc.), an aryl group (e.g., phenyl, 4-methylphenyl, naphthyl, etc.), etc.

The hydrocarbon group and heterocyclic group as the substituent of the heterocyclic group in R may be substituted at any possible position. When the hydrocarbon group contains an alicyclic group or the heterocyclic group is saturated, the alicyclic or heterocyclic group may be substituted by 1 to 3 lower alkyl groups having 1 to 3 carbon atoms (e.g., methyl, ethyl, propyl, isopropyl) on the ring-constituting atoms which may be a nitrogen atom. When the hydrocarbon group contains an aromatic hydrocarbon group or the heterocyclic group is unsaturated, the hydrocarbon or heterocyclic group may have the same or different 1 to 4 substituents on the ring. Examples of the substituents include halogen (e.g., fluorine, chlorine, iodine), hydroxy, cyano, nitro, trifluoromethyl, lower alkoxy (e.g., alkoxy having 1 to 4 carbon atoms such as methoxy, ethoxy, propoxy, isopropoxy, butoxy, etc.), lower alkyl (e.g., alkyl having 1 to 4 carbon atoms such as methyl, ethyl, propyl, isopropyl, butyl, etc.), lower alkoxycarbonyl (e.g., alkoxycarbonyl having 2 to 4 carbon atoms such as methoxycarbonyl, ethoxycarbonyl, propoxycarbonyl, etc.), lower alkylthio (e.g., alkylthio having 1 to 3 carbon atoms such as methylthio, ethylthio, propylthio, isopropylthio, etc.), lower alkylamino (e.g., alkylamino having 1 to 4 carbon atoms such as methylamino, ethylamino, dimethylamino, etc.), etc.

When the heterocyclic group which may be attached through a hydrocarbon chain represented by R is substituted by at least 2 hydrocarbon groups at adjacent positions to each other on the heterocycle, these hydrocarbon groups may be linked together to form a condensed ring. In other words, the two hydrocarbon groups are linked together to form a saturated or unsaturated bivalent chain hydrocarbon group having 3 to 5 carbon groups. Examples of the chain hydrocarbon groups include —CH$_2$CH$_2$CH$_2$—, —CH$_2$CH$_2$CH$_2$CH$_2$—, —CH$_2$CH$_2$CH$_2$CH$_2$CH$_2$—, —CH=CHCH$_2$—, —CH=CH—CH=CH—, —CH=CH—CH=CH—CH$_2$—, —CH=CH—CH$_2$CH$_2$CH$_2$—, etc.

Preferably, the heterocyclic group in R is represented by the formula:

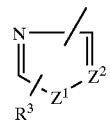

wherein $Z^1$ is a sulfur atom, an oxygen atom or $NR^4$ [in which $R^4$ is a hydrogen atom, a lower alkyl group (e.g., alkyl having 1 to 3 carbon atoms such as methyl, ethyl, etc.) or an aralkyl group (e.g., benzyl, phenethyl, etc.)]; $Z^2$ is a nitrogen atom or C—$R^5$ (in which $R^5$ is a hydrogen atom, optionally substituted hydrocarbon group or optionally substituted heterocyclic group); $R^3$ is a hydrogen atom, optionally substituted hydrocarbon group or optionally substituted heterocyclic group; $R^3$ and $R^5$ may be linked together to form a condensed ring when $R^3$ and $R^5$ are attached to adjacent carbon atoms to each other. Examples of the hydrocarbon groups, heterocyclic groups represented by $R^3$ or $R^5$ and their substituents are similar to those described above for the substituents of the heterocyclic group in R.

This heterocyclic group is attached through any possible atom on the ring. Preferably, it is attached through a carbon atom adjacent to the nitrogen atom. For example, when $Z^1$ is $NR^4$ and $Z^2$ is $C-R^5$, it is particularly preferred that the heterocyclic group is attached through $Z^2$.

Particularly preferred heterocyclic groups represented by the above formula are thiazolyl or oxazolyl represented by the formula:

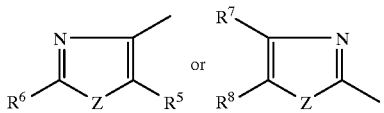

wherein $R^5$ is as defined above, $R^6$, $R^7$ and $R^8$ are the same or different and are a hydrogen atom, an optionally substituted hydrocarbon group or an optionally substituted heterocyclic group, $R^7$ and $R^8$ may be linked together to form a condensed ring, Z is an oxygen atom or sulfur atom.

Examples of the hydrocarbon group, heterocyclic group represented by $R^6$, $R^7$ and $R^8$ and their substituents are similar to those described for the substituents of the heterocyclic group in R. $R^7$ and $R^8$ may be linked together to form a condensed ring. The condensed ring is similar to the above condensed rings which are formed by two hydrocarbon groups at adjacent positions to each other as the substituents of the heterocyclic group.

The hydrocarbon groups in the optionally substituted hydrocarbon groups represented by R in the above formula (I) are similar to those described above for the substituents of the heterocyclic group in R. The substituents are similar to those described above for the substituents of the hydrocarbon group or heterocyclic group as the substituents of the heterocyclic group in R.

Preferably, R is a heterocyclic group which may be attached through a hydrocarbon chain.

The ring containing X as its ring-constituting atom is a benzene ring when X is CH, and a pyridine ring when X is N. In particular, X is preferably CH.

n is 0 or 1. When n is 0, R is directly attached to the benzene or pyridine ring. When n is 1, R is attached to the benzene or pyridine ring through one oxygen atom. n is preferably 1.

The halogen atom, optionally substituted hydroxyl group, and optionally substituted hydrocarbon group represented by $R^1$ or $R^2$ in the above formula (I) are similar to those described above for the substituents of the heterocyclic group in R.

The bivalent hydrocarbon group represented by Y may be aliphatic or aromatic, but is preferably aromatic. The bivalent hydrocarbon group may be straight-chain or branched and saturated or unsaturated, and has preferably 1 to 7 carbon atoms. Examples thereof include saturated bivalent hydrocarbon groups such as $-CH_2-$, $-CH(CH_3)-$, $-(CH_2)_2-$, $-CH(C_2H_5)-$, $-(CH_2)_3-$, $-(CH_2)_4-$, $-(CH_2)_5-$, $-(CH_2)_6-$, $-(CH_2)_7-$, etc.; unsaturated bivalent hydrocarbon groups such as $-CH=CH-$, $-C(CH_3)=CH-$, $-CH=CH-CH_2-$, $-C(C_2H_5)=CH-$, $-CH_2-CH=CH-CH_2-$, $-CH_2-CH_2-CH=CH-CH_2-$, $-CH=CH-CH=CH-CH_2-$, $-CH=CH-CH=CH-CH=CH-CH_2-$, etc. In particular, saturated bivalent hydrocarbon groups having 1 to 4 carbon atoms are preferred, and $-CH_2CH_2-$ is more preferred. Y' in the above formula (I-C5) is as defined for Y, and preferably a bivalent hydrocarbon group having 1 to 5 carbon atoms.

Examples of the bivalent aromatic hydrocarbon groups represented by Y include phenylene, naphthylene, etc. In particular, phenylene is preferred.

Preferred examples of the compound of the formula (I) include:

5-[3-[3-methoxy-4-(5-methyl-2-phenyl-4-oxazolylmethoxy)-phenyl]propyl]-2,4-thiazolidinedione (Example No. 9), 5-[3-[3-fluoro-4-(5-methyl-2-phenyl-4-oxazolylmethoxy)-phenyl]propyl]-2,4-thiazolidinedione (Example No. 10), 5-[3-[4-(5-methyl-2-phenyl-4-oxazolylmethoxy)phenyl]-butyl]-2,4-thiazolidinedione (Example 14), 5-[3-[4-(5-methyl-2-phenyl-4-oxazolylmethoxy)phenyl]-propyl]-2,4-thiazolidinedione (Example 18), and 5-[3-[4-(5-methyl-2-naphthyl-4-oxazolylmethoxy)phenyl]-propyl]-2,4-thiazolidinedione (Example 22).

The salt of the compound of the formula (I) of the present invention is preferably a pharmaceutically acceptable salt. Examples thereof include salts with inorganic bases, organic bases, inorganic acids, organic acids, basic or acidic amino acids, etc.

Preferred examples of the salts with inorganic bases include alkaline metal salts such as a sodium salt, potassium salt, etc., alkaline earth metal salts such as a calcium salt, magnesium salt, etc., an aluminium salt, an ammonium salt, etc.

Preferred examples of the salts with organic bases include salts with trimethylamine, triethylamine, pyridine, picoline, ethanolamine, diethanolamine, triethanolamine, dicyclohexylamine, N,N'-dibenzylethylenediamine, etc.

Preferred examples of the salts with inorganic acids include salts with hydrochloric acid, hydrobromic acid, nitric acid, sulfuric acid, phosphoric acid, etc.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with arginine, lysine, ornithine, etc.

Preferred examples of the salts with acidic amino acids include aspartic acid, glutamic acid, etc.

In particular, a sodium salt or potassium salt is preferred.

The compound (I) (i.e., the compound of the formula (I); hereinafter compounds of other formulas sometimes be abbreviated likewise) or a pharmaceutically acceptable salt thereof of the present invention has low toxicity, and has hypoglycemic activity, blood lipid lowering activity, and insulin sensitivity enhancing activity. The compound (I) or a pharmaceutically acceptable salt thereof can be administered as such or as a mixture with a per se known pharmacologically acceptable carrier including excipient, bulking agent, etc., to mammals such as humans, mice, rats, cats, dogs, rabbits, bovines, swine, sheep and monkeys. Thus, it is useful as antidiabetic or hypotensive agent.

The compound (I) of the present invention has low toxicity. For example, when the compound prepared in Example 14 was orally administered to mice in a daily dose of 15 mg/kg for 4 days, there were no abnormal changes of the body weight and liver weight from those of a control.

Normally, the compound (I) or a salt thereof can orally be administered as tablets, capsules including soft capsules and microcapsules, powders, granules, etc. In some cases, it can parenterally be administered as injections, suppositories, pellets, etc. The oral dose for an adult (body weight: about 50 kg) is 0.05 to 10 mg/kg per day. Preferably, this dose is administered 1 to 3 times per day.

The compound (I) or a salt thereof of the present invention can be formulated with a pharmaceutically acceptable carrier and administered orally or parenterally as solid preparations such as tablets, capsules, granules, powders, etc; or liquid preparations such as syrups, injections, etc.

As the pharmaceutically acceptable carrier, various organic or inorganic carrier materials conventionally used for pharmaceutical preparations can be used, and formulated as excipients, lubricants, binders, disintegrators, etc., for solid preparations, or as solvents, solution adjuvants, suspending agents, tonicity agents, buffering agents, soothing agents, etc., for liquid preparations. If necessary, pharmaceutical additives such as antiseptics, antioxidants, colorants, sweetening agents, etc., can be used.

Preferred examples of the excipients include lactose, sucrose, D-mannitol, starch, crystalline cellulose, light anhydrous silicic acid, etc.

Preferred examples of the lubricants include magnesium stearate, calcium stearate, talc, colloidal silica, etc.

Preferred examples of the binders include crystalline cellulose, sucrose, D-mannitol, dextrin, hydroxypropylcellulose, hydroxypropylmethylcellulose, polyvinylpyrrolidone, etc.

Preferred examples of the disintegrators include starch, carboxymethylcellulose, carboxymethylcellulose calcium, croscarmellose sodium, carboxymethyl starch sodium, etc.

Preferred examples of the solvents include water for injection, alcohols, propylene glycol, macrogol, sesame oil, corn oil, etc.

Preferred examples of the solution adjuvants include polyethylene glycol, propylene glycol, D-mannitol, benzyl benzoate, ethanol, trisaminomethane, cholesterol, triethanolamine, sodium carbonate, sodium citrate, etc.

Preferred examples of the suspending agents include surfactants such as stearyl triethanolamine, sodium lauryl sulfate, laurylaminopropionic acid, lecithin, benzalkonium chloride, benzethonium chloride, glyceryl monostearate, etc.; hydrophilic polymers such as polyvinyl alcohol, polyvinyl pyrrolidone, carboxymethylcellulose sodium, methylcellulose, hydroxymethylcellulose, hydroxyethylcellulose, hydroxypropylcellulose, etc.

Preferred examples of the tonicity agents include sodium chloride, glycerin, D-mannitol, etc.

Preferred examples of the buffering agents include buffers such as phosphates, acetates, carbonates, citrates, etc.

Preferred examples of the soothing agents include benzyl alcohol, etc.

Preferred examples of the antiseptics include parahydroxybenzoic acid esters, chlorobutanol, benzyl alcohol, phenethyl alcohol, dehydroacetic acid, sorbic acid, etc.

Preferred examples of the antioxidants include sulfites, ascorbic acid, etc.

The compound (I) can be prepared, for example, as follows.

Method A $$R-(O)_n-\text{Ar}(X)(R^1)(R^2)-Y-CHO \xrightarrow{\text{2,4-Thiazolidinedione}}$$

(II)

-continued $$R-(O)_n-\text{Ar}(X)(R^1)(R^2)-Y-CH=C(S-C(=O)-NH-C(=O))$$

(I-B1)

wherein each symbol is as defined above.

The compound (I-B1) can be prepared by condensing the compound (II) with 2,4-thiazolidinedione in the presence of a base in a solvent.

The solvents include alcohols such as methanol, ethanol, propanol, isopropanol, 2-methoxyethanol, etc.; aromatic hydrocarbons such as benzene, toluene, xylene, etc.; ethers such as ethyl ether, isopropyl ether, dioxane, tetrahydrofuran, etc.; N,N-dimethylformamide; dimethyl sulfoxide; and acetic acid.

The bases include sodium alkoxides (e.g., sodium methoxide, sodium ethoxide, etc.), potassium carbonate, sodium carbonate, sodium hydride, sodium acetate, secondary amines such as piperidine, piperazine, pyrrolidine, morpholine, diethylamine, diisopropylamine, etc.

The amount of the 2,4-thiazolidinedione to be used is 1 to 10 mol, preferably 1 to 5 mol, per mol of the compound (II). The amount of the base to be used is 0.01 to 5 mol, preferably 0.05 to 2 mol, per mol of the compound (II).

The reaction temperature is 0 to 150° C., preferably 20 to 100° C., and the reaction time is 0.5 to 30 hours.

The compound (I-B1) thus obtained can be isolated and purified by conventional separation and purification techniques such as concentration, concentration under reduced pressure, solvent extraction, crystallization, recrystallization, redistribution, chromatography, etc. The compound (I-B1) is sometimes obtained as a mixture of its (E)- and (Z)-isomers with respect to the double bond at the 5-position on the 2,4-thiazolidinedione ring.

Method B $$R-(O)_n-\text{Ar}(X)(R^1)(R^2)-Y-CH_2CH(S-C(=NH)-NH)-C(=O) \longrightarrow$$

(III)

$$R-(O)_n-\text{Ar}(X)(R^1)(R^2)-Y-CH_2CH(S-C(=O)-NH)-C(=O)$$

(I-B2)

wherein each symbol is as defined above.

The compound (I-B2) can be prepared by hydrolyzing the compound (III). This hydrolysis is normally carried out in an appropriate solvent in the presence of water and a mineral acid.

The solvents include alcohols such as methanol, ethanol, propanol, isopropanol, butanol, 2-methoxyethanol, etc., dimethyl sulfoxide, sulfolane, etc., and mixtures thereof. The mineral acids include hydrochloric acid, hydrobromic acid, sulfuric acid, etc.

The amount of the mineral acid to be used is 0.1 to 20 mol, preferably 0.2 to 10 mol, per mol of the compound (III). The water is normally used in large excess based on the compound (III).

The reaction temperature is normally 20 to 150° C., preferably 50 to 120° C., and the reaction time is 0.5 to 50 hours.

The 2,4-thiazolidinedione derivative (I-B2) thus obtained can be isolated and purified by conventional separation and purification techniques such as concentration, concentration under reduced pressure, solvent extraction, crystallization, recrystallization, redistribution, chromatography, etc.

Method C

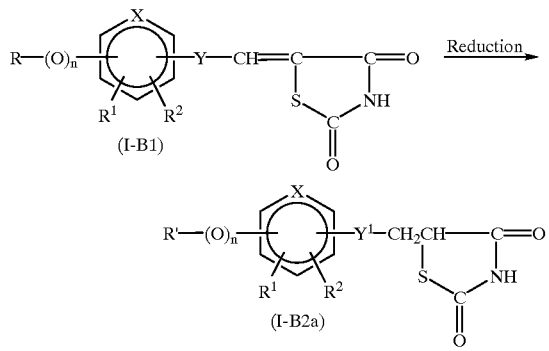

wherein $R^1$ is an optionally substituted hydrocarbon group or a heterocyclic group which may be attached through a saturated hydrocarbon chain, $Y^1$ is a bivalent saturated aliphatic hydrocarbon group and may be linked with $R^1$ or $R^2$ to form a ring, provided that

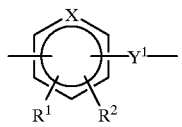

is other than

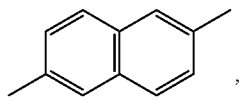

and the other symbols are as defined above.

$Y^1$ is preferably straight-chain or branched bivalent saturated aliphatic hydrocarbon group having 1 to 7 carbon atoms, and can be selected from the above bivalent hydrocarbon groups represented by Y which are aliphatic and saturated.

The optionally substituted hydrocarbon group represented by R' can be selected from that represented by R whose hydrocarbon is saturated.

The heterocyclic groups which may be attached through a saturated hydrocarbon chain represented by R' can be selected from the above heterocyclic groups which may be attached through a hydrocarbon chain represented by R whose hydrocarbon chain is saturated.

The compound (I-B2a) can be prepared by subjecting the compound (1-B1) to reduction. This reduction can be carried out according to a conventional method in a solvent in the presence of a catalyst under an atmosphere of hydrogen at 1 to 150 atm.

The solvents include alcohols such as methanol, ethanol, propanol isopropanol, 2-methoxyethanol, etc., aromatic hydrocarbons such as benzene, toluene, xylene, etc, ethers such as ethyl ether, isopropyl ether, dioxane, tetrahydrofuran, etc, halogenated hydrocarbons such as chloroform, dichloromethane, 1,1,2,2-tetrachloroethane, etc., ethyl acetate, acetic acid, and N,N-dimethylformamide, and mixture thereof. Preferred examples of the catalysts include metals such as nickel compounds, transition metal catalysts such as palladium, platinum, rhodium, etc.

The reaction temperature is 0 to 100° C., preferably 10 to 80° C., and the reaction time is 0.5 to 50 hours.

The 2,4-thiazolidinedione derivative (I-B2a) thus obtained can be isolated and purified by conventional separation and purification techniques such as concentration, concentration under reduced pressure, solvent extraction, crystallization, recrystallization, redistribution, chromatography, etc.

Method D

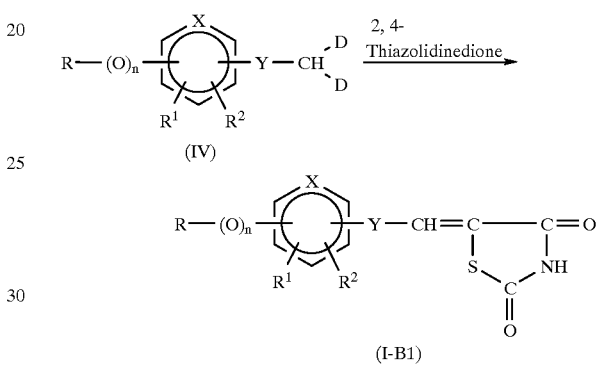

wherein D is a lower alkoxy group, a lower alkylthio group or a lower acyloxy group, and the other symbols are as defined above.

The lower alkoxy groups represented by D include alkoxy groups having 1 to 4 carbon atoms, such as methoxy, ethoxy, propoxy, isopropoxy, butoxy, etc. The lower alkylthio groups include alkylthio groups having 1 to 4 carbon atoms, such as methylthio, ethylthio, propylthio isopropylthio, butylthio, etc. The lower acyloxy groups include acyloxy groups having 1 to 4 carbon atoms, such as acetyloxy, propionyloxy, etc. Two D groups may be linked together to form ethylenedioxy, propylenedioxy, dithiotrimethylene, etc. That is, —CH(D)$_2$ in the formula (IV) represents a protected aldehyde group.

The compound (IV) is condensed with 2,4-thiazolidinedione to give the compound (I-B1). This condensation reaction can be carried out according to the same manner as that described for the reaction of the compound (II) with 2,4-thiazolidinedione in Method A.

Method E

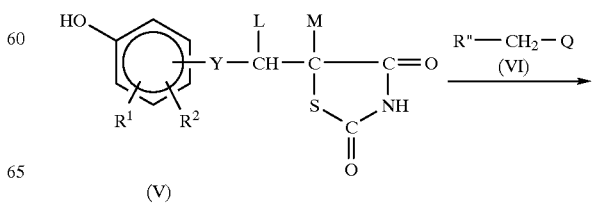

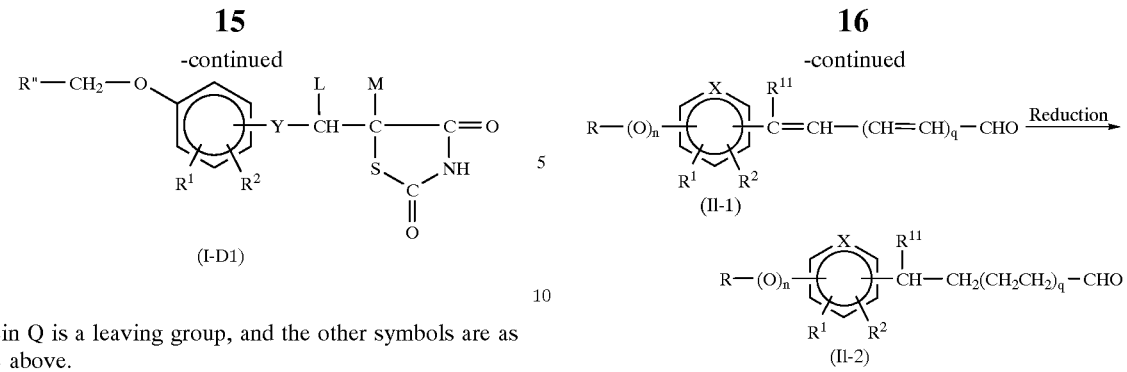

(I-D1)

wherein Q is a leaving group, and the other symbols are as define above.

The leaving groups represented by Q include halogen atoms (e.g., chlorine, bromine, iodine), methanesulfonyloxy, benzenesulfonyloxy, p-toluenesulfonyloxy, etc.

The compound (V) is condensed with the compound (VI) to prepare the compound (I-D1). This reaction is carried out in the presence of a base in an appropriate solvent according to conventional methods.

The solvents include aromatic hydrocarbons such as benzene, toluene, xylene, etc., ethers such as dioxane, tetrahydrofuran, dimethoxyethane, etc., ketones such as acetone, 2-butanone, etc., N,N-dimethylformamide, dimethyl sulfoxide, chloroform, dichloromethane, 1,2-dichloroethane, 1,1,2,2-tetrachloroethane, etc., and mixed solvents thereof.

The bases include alkaline metal salts such as sodium hydroxide, potassium hydroxide, potassium carbonate, sodium bicarbonate, etc., amines such as pyridine, triethylamine, N,N-dimethylaniline, etc., metal hydrides such as sodium hydride, potassium hydride, etc., alkoxides such as sodium ethoxide, sodium methoxide, potassium t-butoxide, etc. The amount of the base to be used is preferably about 1 to 5 mol per mol of the compound (V).

The reaction temperature is normally −50 to 150° C., preferably about −10 to 100° C., and the reaction time is 0.5 to 30 hours.

The compound (I-D1) thus obtained can be isolated and purified by conventional separation and purification techniques such as concentration, concentration under reduced pressure, solvent extraction, crystallization, recrystallization, redistribution, chromatography, etc.

The starting compound (II) in Method A can be prepared, for example, by Method F below.

Method F

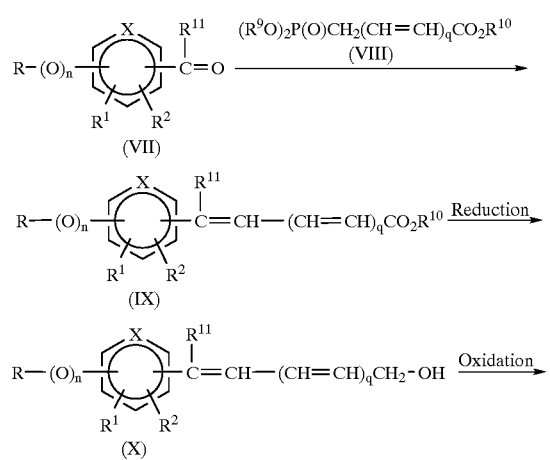

wherein $R^9$ and $R^{10}$ are the same or different and are a lower alkyl group, $R^{11}$ is a hydrogen atom or a lower alkyl group, q is 0, 1 or 2, and the other symbols are as defined above.

The lower alkyl groups represented by $R^9$, $R^{10}$ and $R^{11}$ include alkyl groups having 1 to 4 carbon atoms, such as methyl, ethyl, propyl, isopropyl, butyl, etc.

In this method, firstly, the carbonyl derivative (VII) is reacted with a phosphonoacetic acid derivative or ω-phosphonocarboxylic acid derivative (VIII) to prepare the unsaturated ester derivative (IX). The reaction of the compound (VII) with the compound (VIII) can be carried out in the presence of a base in an appropriate solvent according to conventional methods.

The solvents include aromatic hydrocarbons such as benzene, toluene, xylene, etc., ethers such as dioxane, tetrahydrofuran, dimethoxyethane, etc., alcohols such as methanol, ethanol, propanol, etc., N,N-dimethylformamide, dimethyl sulfoxide, chloroform, dichloromethane, 1,2-dichloroethane, 1,1,2,2-tetrachloroethane, etc., and mixed solvents thereof.

The bases include alkaline metal salts such as sodium hydroxide, potassium hydroxide, potassium carbonate, sodium carbonate, sodium bicarbonate, etc., amines such as pyridine, triethylamine, N,N-dimethylaniline, etc., metal hydrides such as sodium hydride, potassium hydride, etc., alkoxides such as sodium ethoxide, sodium methoxide, potassium t-butoxide, etc.

The amount of the base to be used is preferably about 1 to 5 mol per mol of the compound (VIII). The amount of the compound (VIII) is 1 to 5 mol, preferably about 1 to 3 mol, per mol of the compound (VII).

The reaction temperature is normally −50 to 150° C., preferably about −10 to 100° C., and the reaction time is 0.5 to 30 hours.

Then, the compound (IX) is subjected to reduction to prepare the alcohol derivative (X). This reduction can be carried out according to per se known methods such as reduction with a metal hydride, metal hydride complex compound, diborane or substituted borane. That is, this reaction can be carried out by reacting the compound (IX) with a reducing agent.

The reducing agents include alkaline metal borohydrides (e.g., sodium borohydride, lithium borohydride, etc.), metal hydride complex compounds (e.g., lithium aluminum hydride, diisobutyl aluminum hydride, etc.), and diborane. In particular, diisobutyl aluminum hydride is preferably used.

This reaction is carried out in an organic solvent which does not hinder the reaction. The solvent is appropriately selected depending on the kind of reducing agent from, for example, aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc, alcohols such as methanol, ethanol, propanol, isopropanol, 2-methoxyethanol, etc., amides such as N,N-dimethylformamide, etc., and mixed solvents thereof.

The reaction temperature is −20 to 150° C., preferably about 0 to 100° C., and the reaction time is about 1 to 24 hours.

Then, the compound (X) is subjected to oxidation to prepare the unsaturated carbonyl derivative (II-1). This oxidation can be carried out according to per se known methods such as oxidation with manganese dioxide, chromic acid, dimethyl sulfoxide, etc. That is, this reaction can be carried out by treating the compound (X) with an oxidizing agent. The oxidizing agents include manganese dioxide, chromic anhydride, etc. In particular, manganese dioxide is preferably used.

This reaction is carried out in an organic solvent which does not hinder the reaction. The solvent is appropriately selected depending on the kind of oxidizing agent from, for example, aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc, dimethyl sulfoxide, etc., and mixed solvents thereof.

The reaction temperature is −20 to 150° C., preferably 0 to 100° C., and the reaction time is about 1 to 24 hours.

Then, the compound (II-1) is subjected to reduction to prepare the compound (II-2). This reduction can be carried out according to the same manner as that described in Method C.

The aldehyde derivatives (II-1) and (II-2) thus obtained can be isolated and purified by conventional separation and purification techniques such as concentration, concentration under reduced pressure, solvent extraction, crystallization, recrystallization, redistribution, chromatography, etc.

The starting compound (VII) in Method F can be synthesized by the methods described in, for example, Chemical & Pharmaceutical Bulletin, vol. 39, p. 1440 (1990), JP-A 4-225978, JP-A 61-85372, JP-A 61-271287, JP-A 63-139182, JP-A 3-170478, WO9119496-A1, EP-428312-A, JP-A 1-299289, JP-A 63-230689, etc.

Some of the aldehyde derivatives (VII-1) can also be synthesized, for example, by Method G.

Method G

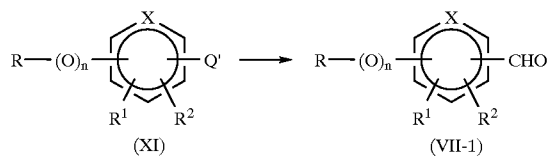

wherein Q' is a halogen atom, and the other symbols are as defined above.

The halogen atoms represented by Q' include, for example, chlorine, bromine, and iodine.

In this method, the compound (XI) is treated with butyllithium, sec-butyllithium, tert-butyllithium, methyllithium, phenyllithium, phenylmagnesium bromide, etc., and then reacted with N,N-dimethylformamide to prepare the compound (VII-1).

The starting material (XI) in Method G can be prepared, for example, by Method H.

Method H

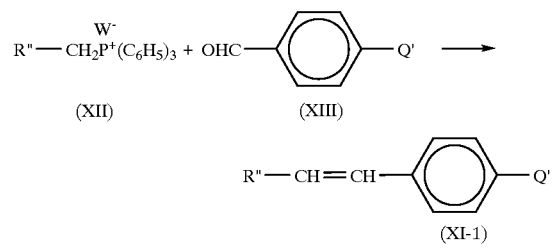

wherein W is a halogen atom, and the other symbols are as defined above.

The halogen atoms represented by W include, for example, chlorine, bromine, and iodine.

In this method, the phosphonium salt (XII) is condensed with the aldehyde derivative (XIII) to prepare the compound (XI-1). This condensation reaction can be carried out according to the same manner as that described for the reaction of the compound (VII) with the compound (VIII) in Method G.

Some of the intermediates of the formula (IX) in Method F can also be prepared, for example, by Method I.

Method I

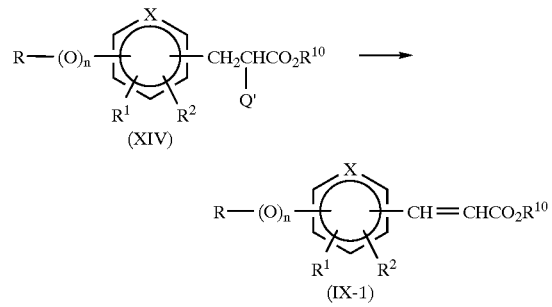

wherein each symbol is as defined above.

This reaction can be carried out in the presence of a base in an appropriate solvent. The solvents include aromatic hydrocarbons such as benzene, toluene, xylene, etc., ethers such as dioxane, tetrahydrofuran, dimethoxyethane, etc., alcohols such as methanol, ethanol, propanol, etc., ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, etc., and mixed solvents thereof.

The bases include inorganic bases such as alkaline metal hydroxides (e.g., sodium hydroxide, potassium hydroxide, etc.), alkaline earth metal hydroxides (e.g., magnesium hydroxide, calcium hydroxide, etc.), alkaline metal carbonates (e.g., sodium carbonate, potassium carbonate, etc.), alkaline earth metal carbonates (e.g., magnesium carbonate, calcium carbonate, etc.), alkaline metal bicarbonate (e.g., sodium bicarbonate, potassium bicarbonate, etc.), alkaline metal acetates (e.g., sodium acetate, potassium acetate, etc.), etc.; organic bases such as trialkylamines (e.g., trimethylamine, triethylamine, etc.), picoline, N-methylpyrrolidine, N-methylmorpholine, 1,5-diazabicyclo[4.3.0]non-5-ene, 1,4-diazabicyclo[2.2.2]non-5-ene, 1,8-diazabicyclo[5.4.0]-7-undecene, etc. The amount of the base to be used is preferably about 1 to 5 mol per mol of the compound (XV).

The reaction temperature is normally −20° C. to 150° C., preferably about −10° C. to 100° C.

The synthesis of the starting compound (XIV) in Method I is described, for example, in Chemical & Pharmaceutical Bulletin, vol. 30, p. 3563 (1982), Chemical & Pharmaceutical Bulletin, vol. 30, p. 3580 (1982), Chemical & Pharmaceutical Bulletin, vol. 32, p. 2267 (1984), Arzneimittel Forschung/Drug Research, vol. 40, p. 37 (1990), Journal of Medicinal Chemistry, vol. 35, p. 2617 (1992), JP-A 61-267580, JP-A 61-286376, JP-A 61-85372, JP-A 2-31079, JP-A 62-5981, etc.

The compound (III) used in Method B can be prepared, for example, by Method J.

Method J

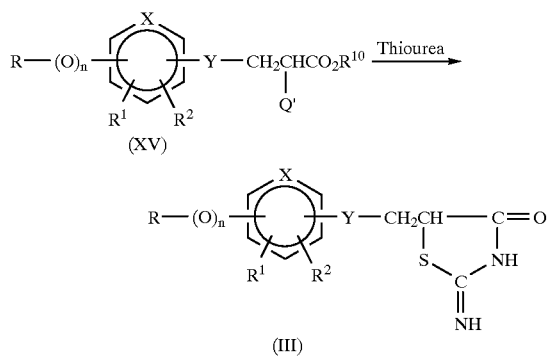

wherein each symbol is as defined above.

The compound (XV) is reacted with thiourea to prepare the compound (III). This reaction is normally carried out in a solvent such as an alcohol (e.g., methanol, ethanol, propanol, 2-propanol, butanol, isobutanol, 2-methoxyethanol, etc.), dimethyl sulfoxide, N,N-dimethylformamide, sulfolane, etc. The reaction temperature is normally 20 to 180° C., preferably 50 to 150° C. The amount of the thiourea to be used is 1 to 2 mol per mol of the compound (XV).

As this reaction proceeds, a hydrogen halide is formed as a by-product. In order to trap this by-product, the reaction may be carried out in the presence of an acid-removing agent such as sodium acetate, potassium acetate, etc. The amount of the acid-removing agent to be used is normally 1 to 1.5 mol per mol of the compound (XV). The compound (III) thus formed can be isolated if necessary, but may directly be used in the acid hydrolysis step without isolation.

The starting compound (IV) in Method D and the starting compound (II) in Method A can be prepared, for example, by Method K.

Method K

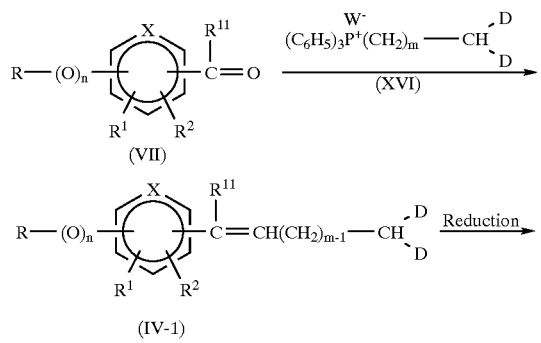

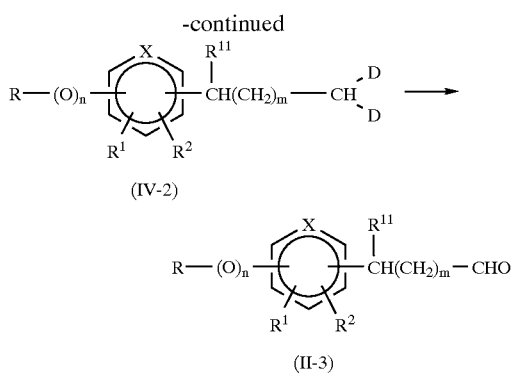

wherein m is an integer of 1 to 6, and the other symbols are as defined above.

In this method, firstly the compound (VII) is condensed with the compound (XVI) to prepare the compound (IV-1). This condensation reaction can be carried out according to the same manner as that described for the reaction of the compound (VII) with the compound (VIII) in Method F.

Then, the compound (IV-1) is subjected to reduction to give the compound (IV-2). This reduction can be carried out according to the same manner as that described for the catalytic hydrogenation of the compound (I-B1) in Method C. The compound (IV-2) is de-protected by treatment with an acid in a water-containing solvent to give the aldehyde derivative (II-4). The solvents include mixed solvents of water with alcohols such as methanol, ethanol, propanol, etc., ethers such as tetrahydrofuran, dioxane, etc., acetonitrile, acetone, 2-butanone, acetic acid, etc. The acids include inorganic acids such as hydrochloric acid, sulfuric acid, nitric acid, hydrobromic acid, etc., organic acids such as p-toluenesulfonic acid, etc.

The starting compound (XV) in Method J can be prepared, for example, by Method L.

Method L

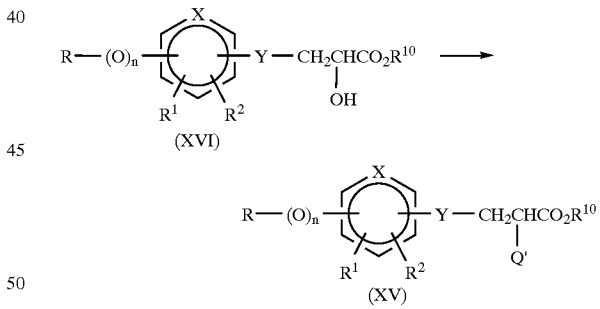

wherein each symbol is as defined above.

The compound (XVI) is reacted with a halogenating agent to prepare the compound (XV). As the halogenating agent, hydrochloric acid, thionyl chloride, phosphorous tribromide, etc., are preferably used. In these cases, the compound (XV) wherein Q' is chloride or bromide is formed. This reaction is carried out at −10 to 80° C. in an appropriate inert solvent (e.g., benzene, toluene, xylene, chloroform, dichloromethane, etc.), or by using an excess halogenating agent as the solvent. The amount of the halogenating agent to be used is 1 to 20 mol per mol of the compound (XVI).

The resulting compound (XV) wherein Q' is chlorine or bromine may be reacted with 1 to 1.5 equivalent of sodium iodide or potassium iodide to give the compound (XV) wherein Q' is iodine. In this case, the reaction can be carried out in a solvent such as acetone, methyl ethyl ketone, methanol, ethanol, etc., at 20 to 80° C.

The starting compound (XVI) in Method L can be prepared, for example, by Method M.

Method M

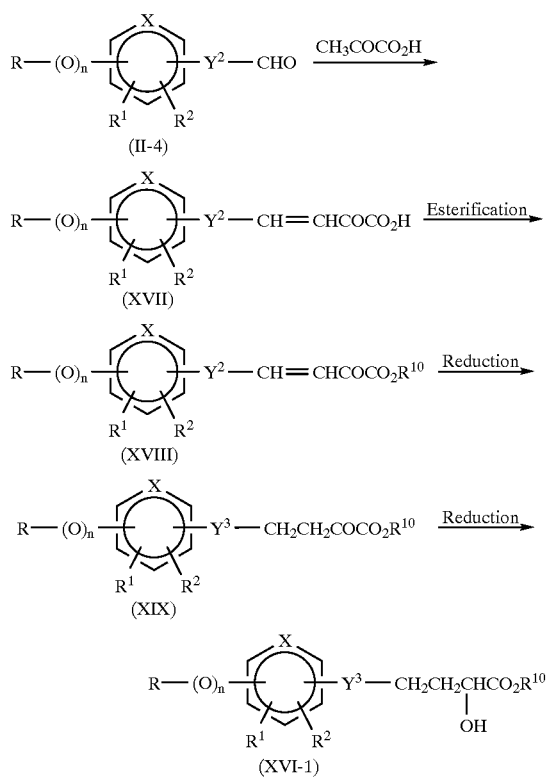

wherein $Y^2$ is a bond or a bivalent aliphatic hydrocarbon group having 1 to 6 carbon atoms, $Y^3$ is a bond or a bivalent saturated aliphatic hydrocarbon group having 1 to 6 carbon atoms, and the other symbols are as defined above.

The bivalent aliphatic hydrocarbon groups having 1 to 6 carbon atoms represented by $Y^2$ mean the bivalent aliphatic hydrocarbon groups represented by Y which have 1 to 6 carbon atoms. The bivalent saturated aliphatic hydrocarbon groups represented by $Y^3$ mean the bivalent aliphatic hydrocarbon groups represented by $Y^2$ which are saturated.

In this method, the compound (II-4) is condensed with pyruvic acid to give the compound (XVII) in a water-containing alcohol in the presence of a base that is selected from the bases described for the reaction of the compound (II) with 2,4-thiazolidinedione in Method A. Then, the compound (XVII) is subjected to esterification to give the compound (XVIII). This esterification can be carried out by per se known methods. For example, the compound (XVII) is reacted with an alcohol ($R^{10}OH$) in the presence of an acid to give the ester. Alternatively, a reactive derivative of the compound (XVII) such as an acid anhydride, acid halide (e.g., acid chloride, acid bromide), imidazolide or mixed acid anhydride (e.g., acid anhydrides with dimethyl carbonate, acid anhydrides with diethyl carbonate, anhydrides with diisobutyl carbonate, etc.) is reacted with an alcohol ($R^{10}OH$) under suitable conditions.

Then, the compound (XVIII) is subjected to catalytic hydrogenation to give the compound (XIX). This catalytic hydrogenation can be carried out according to the same manner as that in Method C.

Then, the compound (XIX) is subjected to reduction to give the compound (XVI-1). This reduction can be carried out by per se known methods such as reduction with metal hydrides, reduction with metal hydride complex compounds, reduction with diborane or substituted borane, catalytic hydrogenation, etc. That is, this reaction can be carried out by treating the compound (XIX) with a reducing agent. The reducing agents include alkaline metal borohydrides (e.g., sodium borohydride, lithium borohydride, etc.), metal hydride complex compounds (e.g., lithium aluminum hydride, etc.), metal hydrides (e.g., sodium hydride, etc.), organic tin compounds (e.g., triphenyltin hydride, etc.), metals and metal salts such as nickel compounds, zinc compounds, etc., transition metal catalysts (e.g., palladium, platinum, rhodium, etc.) and hydrogen for catalytic hydrogenation, diborane, etc. In particular, alkaline metal borohydrides (e.g., sodium borohydride, lithium borohydride, etc.) are preferred.

This reaction is carried out in an organic solvent which does not hinder the reaction. The solvent is appropriately selected depending on the kind of reducing agent from, for example, aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc., alcohols such as methanol, ethanol, propanol, isopropanol, 2-methoxyethanol, etc., amides such as N,N-dimethylformamide, etc., mixed solvents thereof.

The reaction temperature is −20 to 150° C., preferably 0 to 100° C., and the reaction time is about 1 to 24 hours.

As described above, the compound (I) of the present invention or a salt thereof has potent hypoglycemic and blood lipid lowering activity. The following experiment illustrates the activity of the compound (I).

Experiment

Hypoglycemic and lipid lowering activity in mice

A 0.005% mixture of the test compound with powdery feed (CE-2, Charles River Japan Inc.) was fed to KKA$^y$-mice (9 to 14 weeks old) for 4 days without any restriction. Blood was sampled from the orbital veniplex, and glucose and triglyceride in the plasma were quantitated by the enzymatic method using Iatrochem-GLU (A) kit (Yatron) and Iatro-MA701TG kit (Yatron). The results are shown in Table 1. The hypoglycemic activity and lipid lowering activity are indicated as a decrease ratio (%) of the glucose and triglyceride levels in the drug-administered group based on those in the control group, respectively.

TABLE 1

| Compound (Example No.) | Hypoglycemic activity (% reduction) | Lipid-lowering activity (% reduction) |
|---|---|---|
| 9 | 54 | 58 |
| 10 | 36 | 30 |
| 14 | 58 | 61 |
| 18 | 48 | 37 |
| 22 | 53 | 66 |

The results show that the 2,4-thiazolidinedione derivative (I) of the present invention has potent hypoglycemic and lipid-lowering activity, and is useful as a medicament such as an antidiabetic, antilipemic, or hypotensive agent.

The following examples, preparations, and reference examples further illustrate the present invention in detail, but are not to be construed to limit the scope thereof.

EXAMPLE 1

A mixture of 3-(5-methyl-2-phenyl-4-oxazolylmethoxy) cinnamaldehyde (2.4 g), 2,4-thiazolidinedione (1.8 g), piperidine (0.192 g) and ethanol (50 ml) was heated under reflux for 5 hours. After cooling, the precipitated crystals of 5-[3-(5-methyl-2-phenyl-4-oxazolylmethoxy) cinnamilidene]-2,4-thiazolidinedione (1.3 g, 42%) were filtered, and recrystallized from ethyl acetate-methanol. Pale yellow ms, mp: 226–227° C.

Elemental Analysis: Calcd. for $C_{23}H_{18}N_2O_4S$: C,66.01; H,4.34; N,6.69 Found: C,65.91; H,4.26; N,6.64

EXAMPLES 2 TO 4

According to the same manner as that described in Example 1, the compounds in Table 2 were obtained.

Table 2

TABLE 2

| Ex. No. | n | $R^1$ | Yield (%) | mp (° C.) | Recrystallization solvent |
|---|---|---|---|---|---|
| 2 | 2 | H | 24 | 222–223 | Chloroform - Methanol |
| 3 | 1 | $OCH_3$ | 31 | 235–237 | Methanol - Chloroform - Ether |
| 4 | 1 | F | 58 | 258–259 | Chloroform - Ethanol |

EXAMPLE 5

According to the same manner as that described in Example 1, (E)-4-[2-(5-methyl-2-phenyl-4-oxazolyl)vinyl]-cinnamaldehyde was condensed with 2,4-thiazolidinedione to give (E)-5-[4-[2-(5-methyl-2-phenyl-4-oxazolyl)vinyl]-cinnamilidene]-2,4-thiazolidinedione (yield: 33%). This product was recrystallized from N,N-dimethylformamide-water. Yellow needles, mp: not less than 300° C.

EXAMPLE 6

According to the same manner as that described in Example 1, (E)-3-[6-(5-methyl-2-phenyl-4-oxazolylmethoxy)-2-naphthyl]acrolein was condensed with 2,4-thiazolidinedione to give 5-[3-[6-(5-methyl-2-phenyl-4-oxazolylmethoxy)-2-naphthyl]propenylidene]-2,4-thiazolidinedione (yield: 73%). This product was recrystallized from chloroform-methanol. Yellow prisms, mp: 267–268° C.

EXAMPLE 7

A mixture of 5-[3-(5-methyl-2-phenyl-4-oxazolylmethoxy)cinnamilidene]-2,4-thiazolidinedione (0.90 g), palladium-carbon (5%, 2.0 g) and chloroform (200 ml)-methanol (50 ml) was subjected to catalytic hydrogenation at 1 atm at room temperature. The catalyst was filtered off, and the filtrate was concentrated under reduced pressure to give 5-[3-[3-(5-methyl-2-phenyl-4-oxazolylmethoxy)phenyl]propyl]-2,4-thiazolidinedione (0.58 g, 64%). This product was recrystallized from ethyl acetate-hexane. Colorless prisms, mp: 123–124° C.

Elemental Analysis: Calcd. for $C_{23}H_{22}N_2O_4S$: C,65.38; H,5.25; N,6.63 Found: C,65.49; H,5.26; N,6.74

EXAMPLES 8 TO 10

According to the same manner as that described in Example 7, the compounds in Table 3 were obtained.

Table 3

TABLE 3

| Ex. No. | n | $R^1$ | Yield (%) | mp (° C.) | Recrystallization solvent |
|---|---|---|---|---|---|
| 8 | 2 | H | 54 | 151–152 | Ethyl acetate - Hexane |
| 9 | 1 | $OCH_3$ | 48 | 118–120 | Ethylacetate - Ether - Hexane |
| 10 | 1 | F | 97 | 138–139 | Chloroform - Methanol |

EXAMPLE 11

According to the same manner as that described in Example 7, (E)-5-[4-[2-(5-methyl-2-phenyl-4-oxazolyl) vinyl]-cinnamilidene]-2,4-thiazolidinedione was subjected to catalytic hydrogenation to give 5-[3-[4-[2-(5-methyl-2-phenyl-4-oxazolyl)ethyl]phenyl]propyl]-2,4- thiazolidinedione (yield: 22%). This product was recrystallized from ether-hexane. Colorless prisms, mp. 99–100° C.

EXAMPLE 12

According to the same manner as that described in Example 7, 5-[3-[6-(5-methyl-2-phenyl-4-oxazolylmethoxy)-2-naphthyl]propenylidene]-2,4-thiazolidinedione was subjected to catalytic hydrogenation to give 5-[3-[6-(5-methyl-2-phenyl-4-oxazolylmethoxy)-2-naphthyl]propyl]-2,4-thiazolidinedione (yield: 50%). This product was recrystallized from chloroform-ethanol. Pale yellow prisms, mp. 208–209° C.

EXAMPLE 13

A mixture of 2-(5-methyl-2-phenyl-4-oxazolylmethoxy) cinnamaldehyde (2.00 g), 2,4-thiazolidinedione (1.10 g), piperidine (0.267 g) and acetic acid (15 ml) was heated under reflux for 2.5 hours. The reaction mixture was concentrated under reduced pressure. Crystals (1.64 g) of 5-[2-(5-methyl-2-phenyl-4-oxazolylmethoxy)cinnamilidene]-2,4-thiazolidinedione which was precipitated by addition of saturated aqueous sodium bicarbonate solution was collected by filtration and washed with ether. The crystals were dissolved in tetrahydrofuran (150 ml), and 5% palladium-carbon (1.64 g) was added. The mixture was subjected to catalytic hydrogenation at room temperature at a hydrogen pressure of 3.4 kgf/cm$^2$. The catalyst was filtered off, and the filtrate was concentrated under reduced pressure to give crystals. The crystals were recrystallized from dichloromethane-methanol to give 5-[3-[2-(5-methyl-2-phenyl-4-oxazolylmethoxy)phenyl]-propyl]-2,4-thiazolidinedione (0.742 g, 34%). White crystals, mp. 173–174° C.

EXAMPLE 14

According to the same manner as that described in Example 13, (E)-3-[4-(5-methyl-2-phenyl-4-oxazolylmethoxy)-phenyl]-2-butenal was condensed with 2,4-thiazolidinedione, and then the resulting compound was subjected to catalytic hydrogenation to give 5-[3-[4-(5-methyl-2-phenyl-4-oxazolylmethoxy)phenyl]butyl]-2,4-thiazolidinedione (yield: 6%). This product was recrystallized from isopropyl ether. Pale yellow prisms, mp: 64–65° C.

EXAMPLE 15

A mixture of ethyl 2-chloro-4-[4-[2-(5-methyl-2-phenyl-4-oxazolyl)ethoxy]phenyl]butyrate (0.20 g), thiourea (0.145 g), sodium acetate (0.115 g) and ethanol (15 ml) was heated under reflux for 30 hours. 6N hydrochloric acid (15 ml) was added, and the mixture was heated under reflux for 15 hours. The reaction mixture was poured into water, and extracted with ethyl acetate. The ethyl acetate layer was washed with water and dried over magnesium sulfate, and the solvent was evaporated. The residue was subjected to column chromatography on silica gel. The fractions eluted with methanol-chloroform (2:98, v/v) gave 5-[2-[4-[2-(5-methyl-2-phenyl-4-oxazolyl)ethoxy]phenyl]ethyl]-2,4-thiazolidinedione (0.11 g, 56%). This product was recrystallized from dichloromethane-ethanol. Colorless prisms, mp: 151–152° C.

EXAMPLE 16

According to the same manner as that described in Example 15, 5-[2-(4-isopropoxyphenyl)ethyl]-2,4-thiazolidinedione was obtained (yield: 100%) as an oil from ethyl 2-chloro-4-(4-isopropoxyphenyl)butyrate.

NMR (δ ppm in CDCl$_3$): 1.32(6H,d,J=6 Hz), 2.05–2.9 (4H,m), 4.19(1H,dd,J=9.5&4 Hz), 4.4–4.6(1H,m), 6.83(2H, d,J=8.5 Hz), 7.08(2H,d,J=8.5 Hz), 8.29(1H,br s).

EXAMPLE 17

Oily sodium hydride (60%, 0.10 g) was added to a solution of 5-[2-(4-hydroxyphenyl)ethyl]-2,4-thiazolidinedione (0.30 g) in N,N-dimethylformamide (20 ml), and the mixture was stirred at room temperature for 15 minutes. Then, 4-chloromethyl-5-methyl-2-phenyloxazole (0.29 g) was added, and the mixture was stirred at 90 to 100° C. for 2 hours. The reaction mixture was poured into water, acidified with 2N hydrochloric acid and extracted with ethyl acetate. The ethyl acetate layer was washed with water and dried over magnesium sulfate, and the solvent was evaporated. The residue was subjected to column chromatography on silica gel. The fractions eluted with ethyl acetate-chloroform (1:9, v/v) gave 5-[2-[4-(5-methyl-2-phenyl-4-oxazolylmethoxy)phenyl]ethyl]-2,4-thiazolidinedione (0.30 g, 59%). This product was recrystallized from dichloromethane-isopropyl ether. Colorless needles. mp: 146–147° C.

EXAMPLES 18 TO 22

According to the same manner as that described in Example 17, the compounds in Table 4 were obtained.

Table 4

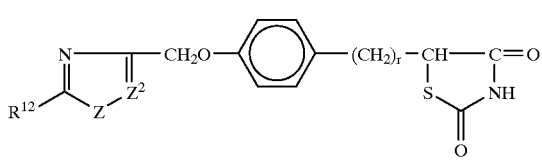

TABLE 2

[Structure: 2-phenyl-5-methyl-oxazole-(CH₂)ₙO-phenyl(R¹)-CH=CHCH=C-thiazolidinedione]

| Ex. No. | n | R¹ | Yield (%) | mp (° C.) | Recrystallization solvent |
|---|---|---|---|---|---|
| 2 | 2 | H | 24 | 222–223 | Chloroform-Methanol |
| 3 | 1 | OCH₃ | 31 | 235–237 | Methanol-Chloroform-Ether |
| 4 | 1 | F | 58 | 258–259 | Chloroform-Ethanol |

EXAMPLE 23

A mixture of 4-isopropoxycinnamaldehyde (6.00 g), 2,4-thiazolidinedione (5.54 g), piperidine (2.69 g) and acetic acid (30 ml) was heated under reflux for 5 hours. The reaction mixture was concentrated under reduced pressure to give precipitated crystals of 5-(4-isopropoxycinnamylidene)-2,4-thiazolidinedione, and the crystals (4.40 g) were collected by filtration and washed with ethyl acetate. The crystals were dissolved in tetrahydrofuran (100 ml), 5% palladium-carbon (2.20 g) was added, and the mixture was subjected to catalytic hydrogenation at room temperature at a hydroaen pressure of 3.8 kgf/cm². The catalyst was filtered off, and the filtrate was concentrated under reduced pressure. The residue was subjected to column chromatography on silica gel. The fractions eluted with ethyl acetate-chloroform (1:9, v/v) gave 5-[3-(4-isopropoxyphenyl)propyl]-2,4-thiazolidinedione (3.61 g, 39%) as an oil.

NMR ($\delta$ ppm in CDCl$_3$): 1.32(6H,d,J=6 Hz), 1.6–2.3(4H, m), 2.61(2H,t,J=7.5 Hz), 4.28(1H,dd,J=8.5&4.5 Hz), 4.4–4.65(1H,m), 6.82(2H,d,J=8.5 Hz), 7.06(2H,d,J=8.5 Hz), 8.34(1H,br s).

EXAMPLE 24

According to the same manner as that described in Example 23, 2-[3-(4-isopropoxyphenyl)propyl]-1,3-dioxolane was condensed with 2,4-thiazolidinedione, and the resulting compound was subjected to catalytic hydrogenation to give crystals of 5-[4-(4-isopropoxyphenyl)butyl]-2,4-thiazolidinedione (yield: 68%). This product was recrystallized from ether-hexane. Colorless prisms, mp: 72–73° C.

EXAMPLE 25

According to the same manner as that described in Example 23, (E,E)-5-(4-isopropoxyphenyl)-2,4-pentadienal was condensed with 2,4-thiazolidinedione, and the resulting compound was subjected to catalytic hydrogenation to give 5-[5-(4-isopropoxyphenyl)pentyl]-2,4-thiazolidinedione as an oil (yield: 26%).

NMR ($\delta$ ppm in CDCl$_3$): 1.2–1.75(6H,m), 1.32(6H,d,J=6 Hz), 1.8–2.3(2H,m), 2.54(2H,t,J=7.5 Hz), 4.26(1H,dd,J=9&4.5 Hz), 4.4–4.6(1H,m), 6.80(2H,d,J=8.5 Hz), 7.05(2H, d,J=8.5 Hz), 8.06(1H,br s).

EXAMPLE 26

According to the same manner as that described in Example 1, 6-(5-methyl-2-phenyl-4-oxazolylmethoxy)-3,4-dihydro-2-naphthoaldehyde was condensed with 2,4-thiazolidinedione to give 5-[6-(5-methyl-2-phenyl-4-oxazolylmethoxy)-3,4-dihydro-2-naphthylmethylidene]-2,4-thiazolidinedione (yield: 50%). This product was recrystallized from dichloromethane-methanol. Yellow needles, mp: 271–272° C.

EXAMPLE 27

According to the same manner as that described in Example 1, (E)-3-methoxy-4-(2-phenyl-4-oxazolylmethoxy)cinnamaldehyde was condensed with 2,4-thiazolidinedione to give 5-[3-methoxy-4-(2-phenyl-4-oxazolylmethoxy)cinnamylidene]-2,4-thiazolidinedione (yield: 57%). This product was recrystallized from chloroform-methanol. Yellow needles, mp: 230–231° C.

EXAMPLE 28

According to the same manner as that described in Example 1, (E)-3-methoxy-4-(2-phenyl-4-thiazolylmethoxy)-cinnamaldehyde was condensed with 2,4-thiazolidinedione to give 5-[3-methoxy-4-(2-phenyl-4-thiazolylmethoxy)-cinnamylidene]-2,4-thiazolidinedione (yield: 49%). This product was recrystallized from chloroform-methanol. Yellow needles, mp: 248–249° C.

EXAMPLE 29

According to the same manner as that described in Example 7, 5-[6-(5-methyl-2-phenyl-4-oxazolylmethoxy)-3,4-dihydro-2-naphthylmethylidene]-2,4-thiazolidinedione was subjected to catalytic hydrogenation to give 5-[6-(5-methyl-2-phenyl-4-oxazolylmethoxy)-1,2,3,4-tetrahydro-2-naphthylmethyl]-2,4-thiazolidinedione (yield: 73%). This product was recrystallized from dichloromethane-methanol. Colorless prisms, mp: 194–195° C.

EXAMPLE 30

According to the same manner as that described in Example 7, 5-[3-methoxy-4-(2-phenyl-4-oxazolylmethoxy)-cinnamylidene]-2,4-thiazolidinedione was subjected to catalytic hydrogenation to give 5-[3-[3-methoxy-4-(2-phenyl-4-oxazolylmethoxy)phenyl]propyl]-2,4-thiazolidinedione (yield: 71%). This product was recrystallized from ethyl acetate-hexane. Colorless prisms, mp: 131–132° C.

EXAMPLE 31

According to the same manner as that described in Example 7, 5-[3-methoxy-4-(2-phenyl-4- thiazolylmethoxy)-cinnamylidene]-2,4-thiazolidinedione was subjected to catalytic hydrogenation to give 5-[3-[3-methoxy-4-(2-phenyl-4-thiazolylmethoxy)phenyl]propyl]-2,4-thiazolidinedione (yield: 57%). This product was recrystallized from ethyl acetate-hexane. Colorless prisms, mp: 123–124° C.

EXAMPLE 32

According to the same manner as that described in Example 13, 4-(5-methyl-2-phenyl-4-oxazolylmethoxy)-3-trifluoromethylcinnamaldehyde was condensed with 2,4-thiazolidinedione, and the resulting product was subjected to catalytic hydrogenation to give 5-[3-[4-(5-methyl-2-phenyl-4-oxazolylmethoxy)-3-trifluoromethylphenyl]propyl]-2,4-thiazolidinedione (yield: 31%). This product was recrystallized from dichloromethane-methanol. Colorless prisms, mp: 154–155° C.

EXAMPLE 33

According to the same manner as that described in Example 13, 3-methoxy-4-[2-(2-furyl)-5-methyl-4-oxazolyl-methoxy]cinnamaldehyde was condensed with 2,4-thiazolidinedione, and the resulting product was subjected to catalytic hydrogenation to give 5-[3-[3-methoxy-4-[2-(2-furyl)-5-methyl-4-oxazolylmethoxy]phenyl]propyl]-2,4-thiazolidinedione (yield: 9%). This product was recrystallized from chloroform-diethyl ether. Colorless prisms, mp: 109–110° C.

EXAMPLE 34

According to the same manner as that described in Example 17, 5-[3-[3-methoxy-4-[2-[(E)-2-phenylethenyl]-4-oxazolylmethoxy]phenyl]propyl]-2,4-thiazolidinedione was obtained (yield: 37%) and recrystallized from chloroform-ethanol. Pale yellow prisms, mp: 154–155° C.

EXAMPLE 35

According to the same manner as that described in Example 17, 5-[3-[3-methoxy-4-[2-[(E)-2-phenylethenyl]-4-thiazolylmethoxy]phenyl]propyl]-2,4-thiazolidinedione was obtained (yield: 30%) and recrystallized from chloroform-ethanol. Pale yellow prisms, mp: 161–162° C.

EXAMPLE 36

According to the same manner as that described in Example 17, 5-[3-[3-methoxy-4-(5-methyl-2-phenyl-4-thiazolylmethoxy)phenyl]propyl]-2,4-thiazolidinedione was obtained (yield: 40%) and recrystallized from ethyl acetate-hexane. Pale yellow needles, mp: 149–150° C.

EXAMPLE 37

According to the same manner as that described in Example 17, 5-[3-[3,5-dimethoxy-4-[2-[(E)-2-phenylethenyl]-4-oxazolylmethoxy]phenyl]propyl]-2,4-thiazolidinedione was obtained (yield: 37%) and recrystallized from ethyl acetate-hexane. Pale yellow prisms, mp: 163–164° C.

EXAMPLE 38

A mixture of 5-[3-[3-methoxy-4-[2-[(E)-2-phenylethenyl]-4-oxazolylmethoxy]phenyl]propyl]-2,4-thiazolidinedione (0.37 g), palladium-carbon (5%, 0.74 g) and tetrahydrofuran (20 ml) was subjected to catalytic hydrogenation at 1 atm and room temperature. The catalyst was filtered off, and the filtrate was concentrated under reduced pressure to give crystals. The crystals were recrystallized from ethyl acetate-hexane to give 5-[3-[3-methoxy-4-(2-phenethyl-4-oxazolylmethoxy)phenyl]propyl]-2,4-thiazolidinedione (0.20 g, 54%). Colorless prisms, mp: 126–127° C.

EXAMPLE 39

According to the same manner as that described in Example 38, 5-[3-[3-methoxy-4-[2-[(E)-2-phenylethenyl]-4-thiazolylmethoxy]phenyl]propyl]-2,4-thiazolidinedione was subjected to catalytic hydrogenation to give 5-[3-[3-methoxy- 4-(2-phenethyl-4-thiazolylmethoxy)phenyl] propyl]-2,4-thiazolidinedione (yield: 59%). This product was recrystallized form ethyl acetate-hexane. Colorless prisms, mp: 104–105° C.

EXAMPLE 40

According to the same manner as that described in Example 1, 4-isopropoxy-3-methoxycinnamaldehyde was condensed with 2,4-thiazolidinedione to give 5-(4-isopropoxy-3-methoxycinnamylidene)-2,4-thiazolidinedione (yield: 61%). This product was recrystallized from ethyl acetate-hexane. Yellow prisms, mp: 230–231° C.

EXAMPLE 41

According to the same manner as that described in Example 1, 4-benzyloxy-3,5-dimethoxycinnamaldehyde was condensed with 2,4-thiazolidinedione to give 5-(4-benzyloxy-3,5-dimethoxycinnamylidene)-2,4-thiazolidinedione (yield: 57%). This product was recrystallized from chloroform-ethanol. Yellow prisms, mp: 217–218° C.

EXAMPLE 42

According to the same manner as that described in Example 7, 5-(4-isopropoxy-3-methoxycinnamylidene)-2,4-thiazolidinedione was subjected to catalytic hydrogenation to give 5-[3-(4-isopropoxy-3-methoxyphenyl)propyl]-2,4-thiazolidinedione as an oil (yield: 75%).

NMR ($\delta$ ppm in CDCl$_3$): 1.35(6H,d,J=6 Hz), 1.65–2.2 (4H,m), 2.62(2H,t,J=7 Hz), 3.85(3H,s), 4.28(1H,dd,J=8&4 Hz), 4.47(1H,m), 6.67(1H,dd,J=8&2 Hz), 6.69(1H,s), 6.83 (1H,d,J=8 Hz), 8.45(1H,br s).

EXAMPLE 43

According to the same manner as that described in Example 7, 5-(4-benzyloxy-3,5-dimethoxycinnamylidene)-2,4-thiazolidinedione was subjected to catalytic hydrogenation to give 5-[3-(4-benzyloxy-3,5-dimethoxyphenyl) propyl]-2,4-thiazolidinedione (yield: 76%). This product was recrystallized from ethyl acetate-hexane. Colorless prisms, mp: 101–102° C.

Preparation 1

| Preparation of Tablets | |
|---|---|
| (1) 5-[3-[4-[2-(5-methyl-2-phenyl-4-oxazolyl)-ethoxy]phenyl]propyl]-2,4-thiazolidinedione | 30 g |
| (2) Lactose | 50 g |
| (3) Corn starch | 15 g |

-continued

Preparation of Tablets

| | |
|---|---:|
| (4) Carboxymethylcellulose calcium | 44 g |
| (5) Magnesium stearate | 1 g |
| 1000 tablets: | 120 g |

Total amounts of (1), (2) and (3) and 30 g of (4) were kneaded with water, dried in vacuo and granulated. The granule powder was mixed with 14 g of (4) and 1 g of (5), and the mixture was tabletted with a tabletting machine to give 1000 tablets each tablet containing 10 mg of (1).

Preparation 2

Preparation of tablets

| | |
|---|---:|
| (1) 5-[3-[3-methoxy-4-(5-methyl-2-phenyl-4-oxazolylmethoxy)phenyl]propyl]-2,4-thiazolidinedione | 10 g |
| (2) Lactose | 50 g |
| (3) Corn starch | 15 g |
| (4) Carboxymethylcellulose calcium | 44 g |
| (5) Magnesium stearate | 1 g |
| 1000 tablets: | 140 g |

Total amounts of (1), (2) and (3) and 30 g of (4) were kneaded with water, dried in vacuo and granulated. The granule powder was mixed with 14 g of (4) and 1 g of (5), and the mixture was tabletted with a tabletting machine to give 1000 tablets each tablet containing 30 mg of (1).

Reference Example 1

Sodium hydride (oily, 60%, 2.40 g) was added little by little to a solution of triethyl phosphonoacetate (12.3 g) in tetrahydrofuran (200 ml) at 0° C., and the mixture was stirred at 10 minutes. Then, 3-(5-methyl-2-phenyl-4-oxazolylmethoxy)benzaldehyde (14.7 g) was added, and the mixture was stirred at 0° C. for 1 hour. The reaction mixture was poured into water and extracted with ethyl acetate. The ethyl acetate layer was washed with water and dried over magnesium sulfate, and the solvent was evaporated under reduced pressure. The residue was subjected to column chromatography on silica gel. The fractions eluted with ethyl acetate-hexane (1:3, v/v) gave crystals of ethyl 3-(5-methyl-2-phenyl-4-oxazolylmethoxy)cinnamate (14.8 g, 81%). The crystals were recrystallized from ethanol. Colorless prisms, mp: 94–95° C.

Elemental Analysis: Calcd. for $C_{22}H_{21}NO_4$: C,72.71; H,5.82; N,3.85 Found: C,72.61; H,5.57; N,3.85

Reference Examples 2 to 6

According to the same manner as the described in Reference Example 1, the compounds in Table 5 were obtained.

TABLE 5

$$\underset{Ph}{\overset{N}{\longrightarrow}}\overset{}{\underset{O}{\longleftarrow}}\overset{}{\underset{Me}{\longrightarrow}}E-G-CH\overset{(E)}{=\!=\!=}CHCO_2R^{10}$$

| Ref. No. | E | G | $R^{10}$ | Yield (%) | mp (° C.) | Recrystallization solvent |
|---|---|---|---|---|---|---|
| 2 | $CH_2CH_2O$ |  | $C_2H_5$ | 88 | 114–115 | Ethyl acetate - Hexane |
| 3 | $CH_2O$ | 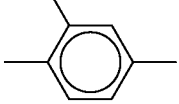 | $CH_3$ | 50 | 135–136 | Ethyl acetate - Ether |
| 4 | CH=CH |  | $C_2H_5$ | 93 | 161–162 | Ethyl acetate |
| 5 | $CH_2O$ | 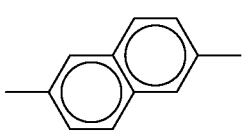 | $C_2H_5$ | 91 | 139–140 | Dichloromethane - Ethanol |

TABLE 5-continued

| Ref. No. | E | G | $R^{10}$ | Yield (%) | mp (° C.) | Recrystallization solvent |
|---|---|---|---|---|---|---|
| 6 | CH$_2$O | (2,3-dimethylphenyl) | CH$_3$ | 77 | 128–129 | Chloroform - Ether |

Reference Example 7

According to the same manner as that described in Reference Example 1, 4-(5-methyl-2-phenyl-4-oxazolylmethoxy)-acetophenone was reacted with trimethyl phosphonoacetate to give methyl (E)-3-[4-(5-methyl-2-phenyl-4-oxazolylmethoxy)-phenyl]-2-butenoate (yield: 54%). This product was recrystallized from ethyl acetate-hexane. Colorless prisms, mp: 125–126° C.

Reference Example 8

According to the same manner as that described in Reference Example 1, 4-isopropoxybenzaldehyde was reacted with triethyl phosphonoacetate to give ethyl 4-isopropoxycinnamate as an oil (yield: 93%).

NMR (δ ppm in CDCl$_3$): 1.33(3H,t,J=7 Hz), 1.35 (6H,d, J=6 Hz), 4.25(2H,q,J=7 Hz), 4.5–4.7(1H,m), 6.30 (1H,d,J=16 Hz), 6.87(2H,d,J=9 Hz), 7.46(2H,d,J=9 Hz), 7.63(1H,d, J=16 Hz).

Reference Example 9

According to the same manner as that described in Reference Example 1, 4-isopropoxybenzaldehyde was reacted with triethyl 4-phosphonocrotonate to give ethyl (E,E)-5-(4-isopropoxyphenyl)pentadienoate as crystals (yield: 58%). The crystals were recrystallized from ether-hexane. Colorless prisms, mp: 64–65° C.

Reference Example 10

A solution of diisobutyl aluminum hydride in toluene (1.5M, 51 ml) was added dropwise to a solution of ethyl 3-(5-methyl-2-phenyl-4-oxazolylmethoxy)cinnamate (14.0 g) in dichloromethane (200 ml) at 0° C. After stirring for 30 minutes, 2N hydrochloric acid (150 ml) was added at 0° C., and the mixture was stirred for 1 hour. The dichloromethane layer was separated, washed with saturated brine and dried over magnesium sulfate. Evaporation of the solvent under reduced pressure gave crystals of (E)-3-[3-(5-methyl-2-phenyl-4-oxazolylmethoxy)phenyl]-2-propenol (11.5 g, 92%). The crystals were recrystallized from ethyl acetate. Colorless prisms, mp: 118–119° C.

Elemental Analysis: Calcd. for $C_{20}H_{19}NO_3$: C,74.75; H,5.96; N,4.36 Found: C,74.78; H,5.76; N,4.39

Reference Examples 11 to 16

According to the same manner as that described in Reference Example 10, the compounds in Table 6 were obtained.

TABLE 6

| Ref. No. | E | G | Yield (%) | mp (° C.) | Recrystallization solvent |
|---|---|---|---|---|---|
| 11 | CH$_2$CH$_2$O | (phenyl) | 90 | 127–128 | Ethyl acetate |

TABLE 6-continued

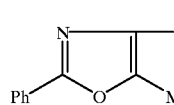

| Ref. No. | E | G | Yield (%) | mp (° C.) | Recrystallization solvent |
|---|---|---|---|---|---|
| 12 | $CH_2O$ | 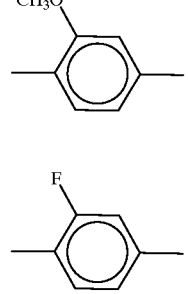 | 88 | 137–138 | Ethyl acetate - Ether |
| 13 | $CH_2O$ | 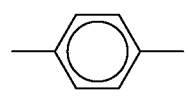 | 80 | 134–135 | Dichloromethane - Isopropyl ether |
| 14 | CH=CH | 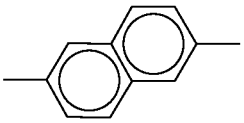 | 96 | 165–166 | Ethyl acetate |
| 15 | $CH_2O$ |  | 91 | 163–164 | Dichloromethane - Ethanol |
| 16 | $CH_2O$ |  | 86 | 128–129 | Ethyl acetate - Chloroform - Ether |

Reference Example 17

According to the same manner as that described in reference Example 10, methyl (E)-3-[4-(5-methyl-2-phenyl-4-oxazolylmethoxy)phenyl]-2-butenoate was reduced with sobutyl aluminum hydride to give (E)-3-[4-(5-methyl-2-phenyl-4-oxazolylmethoxy)phenyl]-2-butenol (yield: 63%). This product was recrystallized from ethyl acetate-ether. colorless crystals, mp: 126–127° C.

Reference Example 18

According to the same manner as that described in Reference Example 10, ethyl 4-isopropoxycinnamate was reduced with diisobutyl aluminum hydride to give (E)-3-(4-isopropoxyphenyl)-2-propenol as an oil. This oil was purified by column chromatography on silica gel (eluent: ethyl acetate-hexane (1:4, v/v)) (yield: 83%).

NMR (δ ppm in CDCl$_3$): 1.33(6H,d,J=6 Hz), 1.38 (1H,t, J=6 Hz), 4.30(2H,td,J=6&1.5 Hz), 4.45–4.65(1H,m), 6.23 (1H,dt,J=16&6 Hz), 6.56(1H,d,J=16 Hz), 6.84(2H,d,J=8.5 Hz), 7.31(2H,d,J=8.5 Hz).

Reference Example 19

According to the same manner as that described in Reference Example 10, ethyl (E,E)-5-(4-isopropoxyphenyl)-2,4-pentadienoate was reduced with diisobutyl aluminum hydride to give crystals of (E,E)-5-(4-isopropoxyphenyl)-2,4-pentadienol (yield: 76%). The crystals were recrystallized from isopropyl ether. Colorless needles, mp: 91–92° C.

Reference Example 20

Activated manganese dioxide (25.0 g) was added to a solution of (E)-3-[3-(5-methyl-2-phenyl-4-oxazolylmethoxy)-phenyl]-2-propenol (11.0 g) in dichloromethane (200 ml), and the mixture was stirred at room temperature for 2 hours. The insoluble materials were filtered off, and the filtrate was concentrated under reduced pressure to give 3-(5-methyl-2-phenyl-4-oxazolylmethoxy) cinnamaldehyde (10.5 g, 96%). This product was recrystallized from ethyl acetate-hexane. Colorless columns, mp: 103–104° C.

Reference Examples 21 to 26

According to the same manner as that described in Reference example 20, the compounds in Table 7 were obtained.

TABLE 7

[Structure: 2-phenyl-5-methyl-oxazole with 4-position substituted by —E—G—CH=CHCHO (E configuration)]

| Ref. No. | E | G | Yield (%) | mp (° C.) | Recrystallization solvent |
|---|---|---|---|---|---|
| 21 | CH$_2$CH$_2$O | [1,4-phenylene] | 94 | 128–129 | Ethyl acetate - Hexane |
| 22 | CH$_2$O | [2-methoxy-1,4-phenylene] | 94 | 136–137 | Ethyl acetate - Ether |
| 23 | CH$_2$O | [2-fluoro-1,4-phenylene] | 90 | 133–134 | Dichloromethane - Methanol |
| 24 | CH=CH | [1,4-phenylene] | 98 | 191–192 | Ethyl acetate |
| 25 | CH$_2$O | [2,6-naphthalenediyl] | 95 | 164–165 | Dichloromethane - Ethanol |
| 26 | CH$_2$O | [2-methyl-1,4-phenylene] | 92 | 112–113 | Chloroform - Isopropyl ether |

Reference Example 27

According to the same manner as that described in Reference Example 20, (E)-3-[4-(5-methyl-2-phenyl-4-oxazolylmethoxy)phenyl]-2-butenol was oxidized with activated maganese dioxide to give (E)-3-[4-(5-methyl-2-phenyl- 4-oxazolylmethoxy)phenyl]crotonaldehyde (yield: 87%). This product was recrystallized from ethyl acetate-ether. Colorless crystals, mp: 94–95° C.

Reference Example 28

According to the same manner as that described in Reference Example 20, (E)-3-(4-isopropoxyphenyl)-2-propenol was oxidized with activated manganese dioxide to give 4-isopropoxycinnamaldehyde as an oil (yield: 89%).

NMR (δ ppm in CDCl$_3$): 1.37(6H,d,J=6 Hz), 4.5–4.7(1H, m), 6.61(1H,dd,J=16&8 Hz), 6.92(2H,d,J=9 Hz), 7.42(1H, d,J=16 Hz), 7.51(2H,d,J=9 Hz), 9.65(1H,d,J=8 Hz).

Reference Example 29

According to the same manner as that described in Reference Example 20, (E,E)-5-(4-isopropoxyphenyl)-2,4-pentadienol was oxidized with activated manganese dioxide to give (E,E)-5-(4-isopropoxyphenyl)-2,4-pentadienal as an oil (yield: 99%).

NMR (δ ppm in CDCl$_3$): 1.36(6H,d,J=6 Hz), 4.5–4.7(1H, m), 6.22(1H,dd,J=15&8 Hz), 6.8–7.05(4H,m), 7.26 (1H,dd, J=15&10 Hz), 7.44(2H,d,J=9 Hz), 9.59(1H,d,J=8 Hz).

Reference Example 30

A solution of sodium carbonate (4.14 g) in water (80 ml) was added dropwise to a solution of 4-[2-(5-methyl-2-phenyl-4-oxazolyl)ethoxy]benzaldehyde (3.0 g) and pyruvic acid (3.44 g) in methanol (80 ml). The mixture was stirred at 70 to 80° C. for 24 hours, and then poured into water and washed with ethyl acetate. The aqueous layer was acidified with conc. hydrochloric acid to collect the precipitated crystals by filtration. The crystals were added to hydrogen chloride-containing ethanol (5%, 15 ml), and the mixture was heated under reflux for 30 minutes. The solvent was evaporated under reduced pressure. The residue was dissolved in chloroform, and the solution was washed with water, dried over magnesium sulfate and concentrated. The residue was purified by column chromatography on silica gel. The fractions eluted with ethyl acetate-chloroform (1:9, v/v) gave ethyl (E)-4-[2-(5-methyl-2-phenyl-4-oxazolyl) ethoxy]benzylidenepyruvate (1.0 g, 25%). This product was recrystallized from dichloromethane-ethanol. Pale yellow needles, mp: 99–100° C.

Reference Example 31

A mixture of ethyl (E)-4-[2-(5-methyl-2-phenyl-4-oxazolyl)ethoxy]benzylidenepyruvate (0.85 g), palladium-carbon (10%, 0.1 g) and dioxane (80 ml) was subjected to catalytic hydrogenation at 1 atm at room temperature. The catalyst was filtered off, and the filtrate was concentrated under reduced pressure. The residue was dissolved in ethanol (20 ml). Sodium borohydride (0.08 g) was added to the solution under ice-cooling, and the mixture was stirred at room temperature for 1 hour. The reaction mixture was poured into water, neutralized with 1N hydrochloric acid and extracted with ethyl acetate. The ethyl acetate layer was washed with water, dried over magnesium sulfate and concentrated. The residue was purified by column chromatography on silica gel. The fractions eluted with chloroform-ethyl acetate (1:9, v/v) gave ethyl 2-hydroxy-4-[4-[2-(5-methyl-2-phenyl-4-oxazolyl)-ethoxy]phenyl]acetate (0.55 g, 64%). This product was recrystallized from ethyl ether-hexane. Colorless needles, mp: 67–68° C.

Reference Example 32

According to the same manner as that described in Reference Example 30, 4-isopropoxybenzaldehyde was condensed with sodium pyruvate, and the resulting compound was esterified to give ethyl (E)-4-isopropoxybenzylidenepyruvate as an oil (yield: 36%).

NMR ($\delta$ ppm in $CDCl_3$): 1.37(6H,d,J=6 Hz), 1.41 (3H,t, J=7 Hz), 4.39(2H,q,J=7 Hz), 4.55–4.75(1H,m), 6.91 (2H,d, J=9 Hz), 7.23(1H,d,J=16 Hz), 7.58(2H,d,J=9 Hz), 7.83 (1H,d,J=16 Hz).

Reference Example 33

A mixture of ethyl (E)-4-isopropoxybenzylidenepyruvate (19.0 g), 5% palladium-carbon (3.00 g) and 20% (v/v) acetic acid-ethanol (500 ml) was subjected to catalytic hydrogenation at 1 atm at room temperature. The catalyst was filtered off, 5% palladium-carbon (3.00 g) was newly added to the filtrate, and catalytic hydrogenation was continued under the same conditions. The catalyst was filtered off, and the filtrate was concentrated under reduced pressure. The residue was subjected to column chromatography on silica gel. The fractions eluted with ethyl acetate-hexane (1:4, v/v) gave ethyl 2-hydroxy-4-(4-isopropoxyphenyl)acetate (11.2 g, 58%) as an oil.

NMR ($\delta$ in $CDCl_3$): 1.29(3H,t,J=7 Hz), 1.32 (6H,d,J=6 Hz), 1.8–2.2(2H,m), 2.65–2.75(2H,m), 2.80 (1H,d,J=5.5 Hz), 4.1–4.25(1H,m), 4.21(2H,q,J=7 Hz), 4.4–4.6(1H,m), 6.81(2H,d,J=8.5 Hz), 7.10(2H,d,J=8.5 Hz).

Reference Example 34

A mixture of ethyl 2-hydroxy-4-[4-[2-(5-methyl-2-phenyl-4-oxazolyl)ethoxy]phenyl]butyrate (320 mg) and thionyl chloride (3 ml) was heated under reflux for 2 hours. The reaction mixture was concentrated under reduced pressure, and the residue was subjected to column chromatography on silica gel. The fractions eluted with ethyl acetate-hexane (1:4, v/v) gave ethyl 2-chloro-4-[4-[2-(5-methyl-2-phenyl-4-oxazolyl)ethoxy]phenyl]butyrate (210 mg, 63%) as an oil.

NMR ($\delta$ in $CDCl_3$): 1.29(3H,t,J=7 Hz), 2.05–2.45(2H,m), 2.38(3H,m), 2.6–2.85(2H,m), 2.97(2H,t,J=6.5 Hz), 4.15–4.3 (5H,m), 6.84(2H,d,J=8.5 Hz), 7.09(2H,d,J=8.5 Hz).

Reference Example 35

According to the same manner as that described in Reference Example 34, ethyl 2-hydroxy-4-(4-isopropoxyphenyl)-butyrate was chlorinated with thionyl chloride to give ethyl 2-chloro-4-(4-isopropoxypheyl) butyrate as an oil (yield: 27%).

NMR ($\delta$ ppm in $CDCl_3$): 1.29(3H,t,J=7 Hz), 1.32 (6H,d, J=6 Hz), 2.1–2.35(2H,m), 2.6–2.9(2H,m), 4.15–4.3(3H,m), 4.4–4.6(1H,m), 6.82(2H,d,J=8.5 Hz), 7.09(2H,d,J=8.5 Hz).

Reference Example 36

Sodium hydride (oily, 60%, 4.60 g) was added little by little to a solution of 2-(1,3-dioxolan-2-yl) ethyltriphenylphosphonium bromide (51.0 g) in N,N-dimethylformamide (200 ml) at 0° C. After stirring for 15 minutes, 4-isopropoxybenzaldehyde (18.0 g) was added, and the mixture was stirred at 80 to 85° C. for 5 hours. Water was added to the reaction mixture, acidified with 2N hydrochloric acid, and extracted with ether. The ether layer was washed with water and dried over magnesium sulfate, and the solvent was evaporated under reduced pressure. The residue was subjected to column chromatography on silica gel. An oil of the intermediate which was obtained from the fractions eluted with ethyl acetate-hexane (1:4, v/v) was dissolved in ethanol (250 ml), and 5% palladium-carbon (5.00 g) was added. The mixture was subjected to catalytic hydrogenation at 1 atm and room temperature. The catalyst was filtered off, and the filtrate was concentrated under reduced pressure. The residue was subjected to column chromatography on silica gel. The fractions eluted with ethyl acetate-hexane (1:5, v/v) to give 2-[3-(4-isopropoxyphenyl) propyl]-1,3-dioxolane (6.70 g, 24%) as an oil.

NMR ($\delta$ ppm in $CDCl_3$): 1.32(6H,d,J=6 Hz), 1.6–1.8(4H, m), 2.5–2.65(2H,m), 3.8–4.0(4H,m), 4.4–4.6(1H,m), 4.8–4.9(1H,m), 6.80(2H,d,J=8.5 Hz), 7.07(2H,d,J=8.5 Hz).

Reference Example 37

Titanium tetrachloride (3.67 g) was added dropwise to a solution of 5-[2-(4-isopropoxyphenyl)ethyl]-2,4-thiazolidinedione (1.35 g) in dichloromethane (70 ml) at 0° C. After stirring for 2 hours, the mixture was poured into ice-cooled water and extracted with ethyl acetate. The ethyl acetate layer was washed with water and dried over magnesium sulfate, and the solvent was evaporated under reduced pressure. The residue was subjected to column chromatography on silica gel. The fractions eluted with ethyl acetate-hexane (1:3, v/v) gave 5-[2-(4-hydroxyphenyl) ethyl]-2,4-thiazolidinedione (0.72 g, 63%). This product was recrystallized from acetone-isopropyl ether. Colorless prisms, mp: 175–176° C.

Elemental Analysis: Calcd. for $C_{11}H_{11}NO_3S$: C,55.68; H,4.67; N,5.90 Found: C,55.63; H,4.57; N,5.83

Reference Examples 38 to 40

According to the same manner as that described in Reference Example 37, the compounds in Table 8 were obtained.

TABLE 8

$$R^{12}\underset{Z}{\overset{N}{\diagdown}}\underset{Z^2}{\overset{}{\diagup}}CH_2O-\!\!\left\langle\phantom{x}\right\rangle\!\!-(CH_2)_r-CH\underset{S}{\overset{}{\diagdown}}\underset{\underset{O}{\overset{}{|}}}{C}\!=\!O$$
$$\phantom{xxxxxxxxxxxxxxxxxxxxxxxxxxxxxxxxxxxxxxxxxxxxxx}NH$$

| Ref. No. | r | Yield (%) | mp (° C.) | Recrystallization solvent |
|---|---|---|---|---|
| 38 | 3 | 57 | 129–130 | Acetone - Isopropyl ether |
| 39 | 4 | 78 | 125–126 | Dichloromethane - Isopropyl ether |
| 40 | 5 | 49 | 112–113 | Acetone - Isopropyl ether |

Reference Example 41

A mixture of 4-chloromethyl-5-methyl-2-phenyloxazole (0.623 g), triphenylphosphine (0.787 g) and acetonitrile (10 ml) was heated under reflux for 24 hours. After cooling, precipitated crystals of (5-methyl-2-phenyl-4-oxazolylmethyl)-triphenylphosphonium chloride (1.25 g, 89%) were obtained. mp. 277–278° C.

Elemental Analysis: Calcd. for $C_{29}H_{25}ClNOP$: C,74.12; H,5.36; N,2.98 Found: C,73.79; H,5.32; N,2.97

Reference Example 42

(5-Methyl-2-phenyl-4-oxazolylmethyl)triphenylphosphonium chloride (25.4 g) was added to a solution of sodium ethoxide in ethanol [prepared from sodium (1.4 g) and ethanol (300 ml)] under cooling. The mixture was stirred at room temperature for 5 minutes, and then 4-bromobenzaldehyde (10.0 g) was added. After stirring at room temperature for 2 hours, the reaction mixture was poured into water and extracted with ethyl acetate. The ethyl acetate layer was washed with water, dried over magnesium sulfate and concentrated under reduced pressure. The residue was subjected to column chromatography on silica gel. The fractions eluted with ether-hexane (1:20, v/v) gave (E)-4-[2-(4-bromophenyl)vinyl]-5-methyl-2-phenyloxazole (13.1 g, 71%). This product was recrystallized from ethyl acetate-hexane. Colorless prisms, mp: 138–139° C.

Reference Example 43

A solution of n-butyllithium in hexane (1.6M, 28.7 ml) was added dropwise to a solution of (E)-4-[2-(4-bromophenyl)vinyl]-5-methyl-2-phenyloxazole (13.0 g) in tetrahydrofuran (140 ml) at −70° C. The mixture was stirred at −70° C. for 15 minutes, and then a solution of N,N-dimethylformamide (4.2 g) in tetrahydrofuran (10 ml) was added dropwise at the same temperature. The reaction mixture was stirred at −70° C. for 30 minutes, and then warmed to room temperature. 1N hydrochloric acid (150 ml) was added dropwise, and the mixture was extracted with ethyl acetate. The ethyl acetate layer was washed with water, dried over magnesium sulfate, and concentrated under reduced pressure. The residue was subjected to column chromatography on silica gel. The fractions eluted with ethyl acetate-hexane (1:2, v/v) gave (E)-4-[2-(5-methyl-2-phenyl-4-oxazolyl)vinyl]-benzaldehyde (5.9 g, 54%). The product was recrystallized from ethyl acetate-hexane. Pale brown prisms, mp: 158–159° C.

Reference Example 44

A mixture of 4-chloromethyl-5-methyl-2-phenyloxazole (9.2 g). p-hydroxyacetophenone (7.9 g), potassium carbonate (6.73 g) and N,N-dimethylformamide (100 ml) was stirred at 70 to 80° C. for 2.5 hours. The mixture was poured into water, and extracted with ethyl acetate. The ethyl acetate layer was washed with water, dried over magnesium sulfate, and concentrated under reduced pressure to give 4-(5-methyl-2-phenyl-4-oxazolylmethoxy)acetophenone (11.6 g, 85%). This product was recrystallized from ethyl acetate-ether. Colorless prisms, mp: 126–127° C.

Reference Example 45

A mixture of methyl 2-bromo-3-[3-fluoro-4-(5-methyl-2-phenyl-4-oxazolylmethoxy)phenyl]propionate (14.2 g), 1,8-diazabicyclo[5.4.0]-7-undecene (DBU) (4.83 g) and toluene (150 ml) was stirred at 80 to 90° C. for 2 hours, and then poured into 2N hydrochloric acid and extracted with ethyl acetate. The ethyl acetate layer was washed with water, dried over magnesium sulfate, and concentrated under reduced pressure to give methyl3-fluoro-4-(5-methyl-2-phenyl-4-oxazolylmethoxy)-cinnamate (10.0 g, 86%). This product was recrystallized from dichloromethane-methanol. Colorless prisms, mp: 167–168° C.

Reference Example 46

According to the same manner as that described in Reference Example 45, methyl 2-bromo-3-[4-(5-methyl-2-phenyl-4-oxazolylmethoxy)-3-trifluoromethylphenyl] propionate was debrominated to give methyl 4-(5-methyl-2-phenyl-4-oxazolylmethoxy)-3-trifluoromethylcinnamate (yield: 80%). This product was recrystallized from ethyl acetate-hexane. Colorless prisms, mp: 148–149° C.

Reference Example 47

According to the same manner as that described in Reference Example 1, 3-methoxy-4-[2-(2-furyl)-5-methyl-4-oxazolylmethoxy]benzaldehyde was reacted with trimethyl phosphonoacetate to give methyl 3-methoxy-4-[2-(2-furyl)-5-methyl-4-oxazolylmethoxy]cinnamate (yield: 90%). This product was recrystallized from dichloromethane-diethyl ether. Colorless prisms, mp: 129–130° C.

Reference Example 48

According to the same manner as that described in Reference Example 1, 3-methoxy-4-(2-phenyl-4-oxazolylmethoxy)-benzaldehyde was reacted with triethyl phosphonoacetate to give ethyl 3-methoxy-4-(2-phenyl-4-oxazolylmethoxy)cinnamate (yield: 96%). This product was recrystallized from ethyl acetate-hexane. Colorless needles, mp: 128–129° C.

Reference Example 49

According to the same manner as that described in Reference Example 1, 3-methoxy-4-(2-phenyl-4-thiazolylmethoxy)benzaldehyde was reacted with triethyl phosphonoacetate to give ethyl 3-methoxy-4-(2-phenyl-4-thiazolylmethoxy)cinnamate (yield: 93%). This product was recrystallized from ethyl acetate-hexane. Colorless needles, mp: 92–93° C.

Reference Example 50

According to the same manner as that described in Reference Example 1, 4-isopropoxy-3-methoxybenzaldehyde was reacted with triethyl phosphonoacetate to give ethyl 4-isopropoxy-3-methoxycinnamate (yield: 91%). This product was recrystallized from ethyl acetate-hexane. Colorless prisms, mp: 103–104° C.

Reference Example 51

According to the same manner as that described in Reference Example 1, 4-benzyloxy-3,5-dimethoxybenzaldehyde was reacted with triethyl phosphonoacetate to give ethyl 4-benzyloxy-3,5-dimethoxycinnamate (yield: 96%). This product was recrystallized from diethyl ether-hexane. Colorless plates, mp: 68–69° C.

Reference Example 52

According to the same manner as that described in Reference Example 10, methyl 4-(5-methyl-2-phenyl-4-oxazolylmethoxy)-3-trifluoromethylcinnamate was reduced to give (E)-3-[4-(5-methyl-2-phenyl-4-oxazolylmethoxy)-3-trifluoromethyl-phenyl]-2-propenol (yield: 87%). This product was recrystallized from dichloromethane-isopropyl ether. Colorless prisms, mp: 152–153° C.

Reference Example 53

According to the same manner as that described in Reference Example 10, methyl 3-methoxy-4-[2-(2-furyl)-5-methyl-4-oxazolylmethoxy)cinnamate was reduced to give (E)-3-[3-methoxy-4-[2-(2-furyl)-5-methyl-4-oxazolylmethoxy]phenyl]-2-propenol (yield: 84%). This product was recrystallized from dichloromethane-diethyl ether. Colorless needles, mp: 128–129° C.

Reference Example 54

According to the same manner as that described in Reference Example 10, ethyl 3-methoxy-4-(2-phenyl-4-oxazolylmethoxy)cinnamate was reduced to give (E)-3-[3-methoxy-4-(2-phenyl-4-oxazolylmethoxy)phenyl]-2-propenol (yield: 98%). This product was recrystallized from ethyl acetate-hexane. Colorless needles, mp: 113–114° C.

Reference Example 55

According to the same manner as that described in Reference Example 10, ethyl 3-methoxy-4-(2-phenyl-4-thiazolylmethoxy)cinnamate was reduced to give (E)-3-[3-methoxy-4-(2-phenyl-4-thiazolylmethoxy)phenyl]-2-propenol (yield: 86%). This product was recrystallized from ethyl acetate-hexane. Colorless prisms, mp: 71–72° C.

Reference Example 56

A solution of aluminium chloride ($AlCl_3$) (6.1 g) in diethyl ether (70 ml) was added dropwise to a suspension of lithium aluminum hydride ($LiAlH_4$) (6.4 g) in diethyl ether (270 ml) at 0° C., and the mixture was stirred at room temperature for 10 minutes. Then, a solution of ethyl 4-isopropoxy-3-methoxycinnamate (35.4 g) in diethyl ether-tetrahydrofuran (3:1, 220 ml) was added dropwise at room temperature. The mixture was stirred at room temperature for 2 hours. Then water (170 ml) and 6N sulfuric acid (270 ml) were added dropwise under ice-cooling, and the organic layer was separated, and the aqueous layer was extracted with diethyl ether. The organic layers were combined, washed with water, dried over magnesium sulfate, and concentrated. The residue was subjected to chromatography on silica gel. The fractions eluted with ethyl acetate-hexane (1:2, v/v) gave (E)-3-(4-isopropoxy-3-methoxyphenyl)-2-propenol (27.0 g, 91%) as an oil.

NMR (δ ppm in $CDCl_3$): 1.37(6H,d,J=6 Hz), 1.52(1H,s), 3.87(3H,s), 4.30(2H,dd,J=6&1 Hz), 4.52(1H,m), 6.24(1H, dd, J=16&6 Hz), 6.55(1H,d,J=16 Hz), 6.83(1H,d,J=8 Hz), 6.90(1H,dd, J=8&2 Hz), 6.94(1H,d,J=2 Hz).

Reference Example 57

According to the same manner as that described in Reference Example 56, ethyl 4-benzyloxy-3,5-dimethoxycinnamate was reduced to give (E)-3-(4-benzyloxy-3,5-dimethoxyphenyl)-2-propenol (yield: 91%). This product was recrystallized from ethyl acetate-hexane. Colorless needles, mp: 72–73° C.

Reference Example 58

According to the same manner as that described in Reference Example 20, (E)-3-[4-(5-methyl-2-phenyl-4-oxazolylmethoxy)-3-trifluoromethylphenyl]-2-propenol was oxidized to give 4-(5-methyl-2-phenyl-4-oxazolylmethoxy)-3-trifluoromethylcinnamaldehyde (yield: 89%). This product was recrystallized from dichloromethane-isopropyl ether. Colorless prisms, mp: 138–139° C.

Reference Example 59

According to the same manner as that described in Reference Example 20, (E)-3-[3-methoxy-4-[2-(2-furyl)-5-methyl-4-oxazolylmethoxy]phenyl]-2-propenol was oxidized to give 3-methoxy-4-[2-(2-furyl)-5-methyl-4-oxazolylmethoxy]-cinnamaldehyde (yield: 94%). This product was recrystallized from dichloromethane-diethyl ether. Colorless prisms, mp: 125–126° C.

Reference Example 60

According to the same manner as that described in Reference Example 20, (E)-3-[3-methoxy-4-(2-phenyl-4-oxazolylmethoxy)phenyl]-2-propenol was oxidized to give 3-methoxy-4-(2-phenyl-4-oxazolylmethoxy)cinnamaldehyde (yield: 88%). This product was recrystallized from ethyl acetate-hexane. Colorless needles, mp: 144–145° C.

Reference Example 61

According to the same manner as that described in Reference Example 20, (E)-3-[3-methoxy-4-(2-phenyl-4-thiazolylmethoxy)phenyl]-2-propenol was oxidized to give 3-methoxy-4-(2-phenyl-4-thiazolylmethoxy)cinnamaldehyde (yield: 80%). This product was recrystallized from ethyl acetate-hexane. Colorless prisms, mp: 115–116° C.

Reference Example 62

According to the same manner as that described in Reference Example 20, (E)-3-(4-isopropoxy-3-methoxyphenyl)-2-propenol was oxidized to give 4-isopropoxy-3-methoxycinnamaldehyde (yield: 90%). This product was recrystallized from ethyl acetate-hexane. Colorless plates, mp: 93–94° C.

Reference Example 63

According to the same manner as that described in Reference Example 20, (E)-3-(4-benzyl-3,5-dimethoxyphenyl)- 2-propenol was oxidized to give 4-benzyloxy-3,5-dimethoxycinnamaldehyde (yield: 93%). This product was recrystallized from ethyl acetate-hexane. Colorless plates, mp: 114–115° C.

Reference Example 64

According to the same manner as that described in Reference Example 37, 5-[3-(4-isopropoxy-3-methoxyphenyl)-propyl]-2,4-thiazolidinedione was treated with titanium tetrachloride to give 5-[3-(4-hydroxy-3-methoxyphenyl)propyl]-2,4-thiazolidinedione as an oil (yield: 87%).

NMR (δ ppm in CDCl$_3$): 1.65–2.2(4H,m), 2.61(2H,t, J=7 Hz), 3.89(3H,s), 4.28(1H,dd,J=9&4 Hz), 5.51(1H,s), 6.66 (1H,dd,J=9&2 Hz), 6.66(1H,d,J=2 Hz), 6.84(1H,d,J=9 Hz), 8.37 (1H,br s).

Reference Example 65

According to the same manner as that described in Reference Example 37, 5-[3-(4-benzyloxy-3,5-dimethoxyphenyl)-propyl]-2,4-thiazolidinedione was treated with titanium tetrachloride to give 5-[3-(4-hydroxy-3,5-dimethoxyphenyl)-propyl]-2,4-thiazolidinedione as an oil (yield: 82%).

NMR (δ ppm in CDCl$_3$): 1.75–2.15(4H,m), 2.61 (2H,t, J=7 Hz), 3.88(6H,s), 4.29(1H,dd,J=8&4 Hz), 5.42(1H,s), 6.39(2H,s).

Reference Example 66

A mixture of 4-chloromethyl-5-methyl-2-phenyloxazole (19.2 g), 6-hydroxytetralone (15.0 g), potassium carbonate (15.4 g) and dimethylformamide (DMF) (100 ml) was stirred at 80 to 90° C. for 2 hours. The reaction mixture was poured into water, and the precipitated crystals of 6-(5-methyl-2-phenyl-4-oxazolylmethoxy)tetralone (29.5 g, 96%) were collected by filtration and recrystallized from dichloromethane-methanol. Colorless prisms, mp: 143–144° C.

Reference Example 67

Sodium methoxide (28%, 43.4 g) was concentrated to dryness, and a solution of 6-(5-methyl-2-phenyl-4-oxazolymethoxy)tetralone (15.0 g) and dimethyl carbonate (81.0 g) in tetrahydrofuran (THF) (40 ml) was added dropwise at room temperature with stirring. After heating under reflux for 1 hour, conc. hydrochloric acid was added at 0° C., and the mixture was extracted with ethyl acetate. The organic layer was washed with water, dried over magnesium sulfate, and concentrated. The residue was subjected to column chromatography on silica gel. The fractions eluted with ethyl acetate-chloroform (2:98, v/v) gave an oil (17.6 g). This oil was dissolved in THF (40 ml)-methanol (120 ml), and sodium borohydride (850 mg) was added little by little at 0° C. After stirring for 2 hours, the reaction mixture was poured into 2N hydrochloric acid, and the mixture was extracted with ethyl acetate. The organic layer was washed with water, dried over magnesium sulfate, and concentrated. The residue was subjected to column chromatography on silica gel. The fractions eluted with ethyl acetate-chloroform (2:98, v/v) gave methyl 1-hydroxy-6-(5-methyl-2-phenyl-4-oxazolylmethoxy)-1,2,3,4-tetrahydronaphthalene-2-carboxylate (5.77 g, 33%). This product was recrystallized from dichloromethane-methanol. Colorless prisms, mp: 146–147° C.

Reference Example 68

Boron trifluoride diethyl ether complex (4.14 g) was added dropwise to a solution of methyl 1-hydroxy-6-(5-methyl-2-phenyl-4-oxazolylmethoxy)-1,2,3,4-tetrahydronaphthalene-2-carboxylate (5.46 g) in dichloromethane (200 ml) at 0° C. The mixture was stirred at room temperature for 1 hour. Then, the reaction mixture was washed with water, dried over magnesium sulfate, and concentrated. The residue was subjected to column chromatography on silica gel. The fractions eluted with chloroform gave methyl 6-(5-methyl-2-phenyl-4-oxazolylmethoxy)-3,4-dihydronaphthalene-2-carboxylate (4.30 g, 83%). This product was recrystallized from dichloromethane-isopropyl ether. Colorless prisms, mp: 130–131° C.

Reference Example 69

According to the same manner as that described in Reference Example 10, methyl 6-(5-methyl-2-phenyl-4-oxazolylmethoxy)-3,4-dihydronaphthalene-2-carboxylate was reduced to give 6-(5-methyl-2-phenyl-4-oxazolylmethoxy)-3,4-dihydro-2-naphthylmethanol. This product was recrystallized from acetone-isopropyl ether. Colorless prisms, mp: 141–142° C.

Reference Example 70

According to the same manner as that described in Reference Example 20, 6-(5-methyl-2-phenyl-4-oxazolylmethoxy-3,4-dihydro-2-naphthylmethanol was oxidized to give 6-(5-methyl-2-phenyl-4-oxazolylmethoxy)-3,4-dihydro-2-naphthoaldehyde. This product was recrystallized from dichloromethane-isopropyl ether. Colorless prisms, mp: 114–115° C.

Reference Example 71

Methylhydrazine (3.49 g) was added dropwise to a solution of methyl benzimidate hydrochloride in methanol (80 ml) at 0° C. After stirring for 3 hours, the reaction mixture was concentrated to give 2-methyl-3-phenylamidrazone hydrochloride (12.5 g, 89%). This product was recrystallized from methanol-diethyl ether. Colorless prisms, mp: 197–198° C.

Reference Example 72

A mixture of 2-methyl-3-phenylamidrazone hydrochloride (3.15 g), chloroacetyl chloride (1.92 g) and benzene (40 ml) was heated under reflux for 2 hours with stirring. Ethyl acetate was added to the reaction mixture, and the mixture was washed with water, dried over magnesium sulfate, and concentrated to give 3-chloromethyl-1-methyl-5-phenyl-1H-triazole (1.00 g, 28%). This product was recrystallized from diethyl ether-hexane. Colorless prisms, mp: 112–113° C.

We claim:

1. A 2,4-thiazolidinedione derivative of the formula (I):

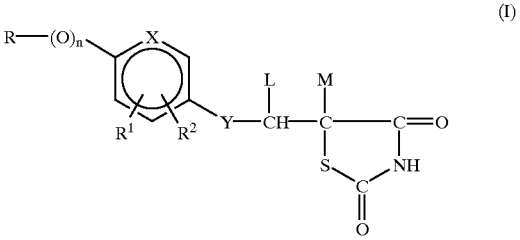

wherein:

R is a 1,3-oxazolyl which may be attached through a hydrocarbon chain having 1 to 8 carbon atoms selected from an alkylene group, an alkenylene group, an alkadienylene group or an alkatrienylene group and optionally having at least one substituent selected from:
(a) a $C_{1-8}$ aliphatic hydrocarbon group selected from an alkyl group, an alkenyl group or an alkynyl group;
(b) a $C_{3-7}$ alicyclic hydrocarbon group selected from a cycloalkyl group or a cycloalkenyl group;
(c) a $C_{4-9}$ alicyclic-aliphatic hydrocarbon group selected from a cycloalkyl-alkyl group or a cycloalkenyl-alkyl group;
(d) a $C_{7-9}$ phenylalkyl, a $C_{11-13}$ naphthylalkyl or 2-phenylethenyl;
(e) an aromatic hydrocarbon group selected from phenyl or naphthyl;
(f) an amino group;
(g) a N-monosubstituted amino group having a substituent selected from (1) a $C_{1-4}$ alkyl group, (2) a $C_{3-7}$ cycloalkyl group, (3) an aryl group selected from phenyl or naphthyl, (4) an aralkyl group selected from benzyl or phenethyl, (5) an acyl group selected from acetyl or propionyl, (6) a carbamoyl group, (7) N-monosubstituted carbamoyl group selected from N-methylcarbamoyl, N-ethylcarbamoyl or N-propylcarbamoyl, (8) N,N-disubstituted carbamoyl group selected from N,N-dimethylcarbamoyl, N-methyl-N-ethylcarbamoyl or N,N-diethylcarbamoyl, (9) a $C_{2-5}$ alkoxycarbonyl group, (10) a hydroxy group, (11) a $C_{1-4}$ alkoxy group or (12) an aralkyloxy group selected from benzyloxy, phenethyloxy or naphthyl-methyloxy; or
(h) a N,N-disubstituted amino group having a first substituent selected from groups (1) to (12) defined above with respect to the N-monosubstituted amino group, and having a second substituent selected from (13) a $C_{1-4}$ alkyl group, (14) a $C_{3-7}$ cycloalkyl group, (15) an aryl group selected from phenyl or naphthyl or (16) an aralkyl group selected from benzyl or phenethyl, wherein the first and second substituents may be linked together with the nitrogen atom to form a cyclic amino group; wherein groups (b) and (c) may be substituted by 1 to 3 $C_{1-4}$ alkyl groups; and wherein groups (d) and (e) may have 1 to 4 substituents selected from halogen, hydroxy, cyano, nitro, trifluoromethyl, $C_{1-4}$ alkoxy, $C_{1-4}$ alkyl, $C_{2-5}$ alkoxycarbonyl, $C_{1-3}$ alkylthio or $C_{1-4}$ alkylamino;
n is 1;
X is CH;
Y is a $C_{2-7}$ alkylene group;
$R^1$ is a hydroxy group, a $C_{1-4}$ alkoxy group, an aralkyloxy group selected from benzyloxy, phenethyloxy or naphthylmethyloxy, or an optionally substituted hydrocarbon group selected from:
(i) a $C_{1-8}$ aliphatic hydrocarbon group selected from an alkyl group, an alkenyl group or an alkynyl group;
(ii) a $C_{3-7}$ alicyclic hydrocarbon group selected from a cycloalkyl group or a cycloalkenyl group;
(iii) a $C_{4-9}$ alicyclic-alihatic hydrocarbon group selected from a cycloalkyl-alkyl group or a cycloalkenyl-alkyl group:
(iv) a $C_{7-9}$ phenylalkyl, a $C_{11-13}$ naphthyalkyl or 2-phenylethenyl; or
(v) an aromatic hydrocarbon group selected from phenyl or naphthyl;
wherein groups (ii) and (iii) may be substituted by 1 to 3 $C_{1-4}$ alkyl groups, and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino;

$R^2$ is a hydrogen atom, a halogen atom, a hydroxy group, a $C_{1-4}$ alkoxy group, an aralkyloxy group selected from benzyloxy, phenethyloxy or naphthylmethyloxy, or an optionally substituted hydrocarbon group selected from:
(i) a $C_{1-8}$ aliphatic hydrocarbon group selected from an alkyl group, an alkenyl group, or an alkynyl group;
(ii) a $C_{3-7}$ alicyclic hydrocarbon group selected from a cycloalkyl group or a cycloalkenyl group;
(iii) a $C_{4-9}$ alicyclic-aliphatic hydrocarbon group selected from a cycloalkyl-alkyl group or a cycloalkenyl-alkyl group;
(iv) a $C_{7-9}$ phenylalkyl, a $C_{11-13}$ naphthylalkyl or 2-phenylethenyl; or
(v) an aromatic hydrocarbon group selected from phenyl or naphthyl;
wherein groups (ii) and (iii) may be substituted by 1 to 3 $C_{1-4}$ alkyl groups, and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino; and
wherein either $R^1$ or $R^2$ and one carbon atom of Y may be linked together to form a ring; provided that

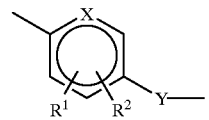

is other than

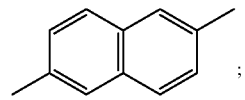

and

L and M are each a hydrogen atom, or L and M are linked together to form a bond;
or a salt thereof.

2. The compound according to claim 1, wherein R is represented by the formula:

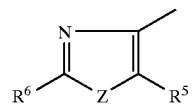

wherein:
$R^5$ and $R^6$ are the same or different and are a hydrogen atom, an optionally substituted hydrocarbon group selected from:
(i) a $C_{1-8}$ aliphatic hydrocarbon group selected from an alkyl group, an alkenyl group or an alkynyl group;
(ii) a $C_{3-7}$ alicyclic hydrocarbon group selected from a cycloalkyl group or a cycloalkenyl group;
(iii) a $C_{4-9}$ alicyclic-aliphatic hydrocarbon group selected from a cycloalkyl-alkyl group and a cycloalkenyl-alkyl group;

(iv) a $C_{7-9}$ phenylalkyl, a $C_{1-13}$ naphthylalkyl or 2-phenylethenyl; or (v) an aromatic hydrocarbon group selected from phenyl or naphthyl;

wherein groups (ii) and (iii) may be substituted by 1 to 3 $C_{1-4}$ alkyl groups; and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino; and Z is an oxygen atom, or a salt thereof.

3. The compound according to claim 1, wherein R is represented by the formula:

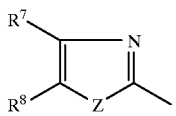

wherein:

Z is an oxygen atom;

$R^7$ and $R^8$ are the same or different and are a hydrogen atom, an optionally substituted hydrocarbon group selected from:

(i) a $C_{1-8}$ aliphatic hydrocarbon group selected from an alkyl group, an alkenyl group or an alkynyl group;

(ii) a $C_{3-7}$ alicyclic hydrocarbon group selected from a cycloalkyl group or a cycloalkenyl group;

(iii) a $C_{4-9}$ alicyclic-aliphatic hydrocarbon group selected from a cycloalkyl-alkyl group or a cycloalkenyl-alkyl group;

(iv) a $C_{7-9}$ phenylalkyl, a $C_{11-13}$ naphthylalkyl or 2-phenylethenyl; or (v) an aromatic hydrocarbon group selected from phenyl or naphthyl;

wherein groups (ii) and (iii) may be substituted by 1 to 3 $C_{1-4}$ alkyl groups; and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio and $C_{1-4}$ alkylamino; or $R^7$ and $R^8$ are linked together to form a ring; or a salt thereof.

4. A pharmaceutical composition which comprises an effective amount of a 2,4-thiazolidinedione derivative of the formula (I):

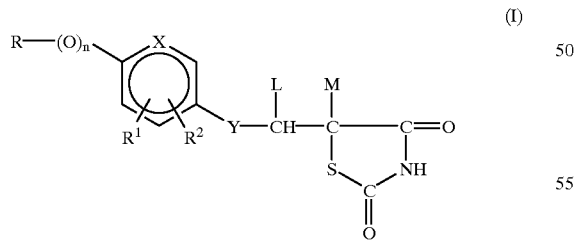

wherein:

R is a 1,3-oxazolyl which may be attached through a hydrocarbon chain having 1 to 8 carbon atoms selected from an alkylene group, an alkenylene group, an alkadienylene group or an alkatrienylene group and optionally having at least one substituent selected from:

(a) a $C_{1-8}$ aliphatic hydrocarbon group selected from an alkyl group, an alkenyl group or an alkynyl group;

(b) a $C_{3-7}$ alicyclic hydrocarbon group selected from a cycloalkyl group or a cycloalkenyl group;

(c) a $C_{4-9}$ alicyclic-aliphatic hydrocarbon group selected from a cycloalkyl-alkyl group or a cycloalkenyl-alkyl group;

(d) a $C_{7-9}$ phenylalkyl, a $C_{11-13}$ naphthylalkyl or 2-phenylethenyl;

(e) an aromatic hydrocarbon group selected from phenyl or naphthyl;

(f) an amino group;

(g) a N-monosubstituted amino group having a substituent selected from (1) a $C_{1-4}$ alkyl group, (2) a $C_{3-7}$ cycloalkyl group, (3) an aryl group selected from phenyl or naphthyl, (4) an aralkyl group selected from benzyl or phenethyl, (5) an acyl group selected from acetyl or propionyl, (6) a carbamoyl group, (7) N-monosubstituted carbamoyl group selected from N-methylcarbamoyl, N-ethylcarbamoyl or N-propylcarbamoyl, (8) N,N-disubstituted carbamoyl group selected from N,N-dimethylcarbamoyl, N-methyl-N-ethylcarbamoyl or N,N-diethylcarbamoyl, (9) a $C_{2-5}$ alkoxycarbonyl group, (10) a hydroxy group, (11) a $C_{1-4}$ alkoxy group or (12) an aralkyloxy group selected from benzyloxy, phenethyloxy or naphthylmethyloxy; or (h) a N,N-disubstituted amino group having a first substituent selected from groups (1) to (12) defined above with respect to the N-monosubstituted amino group, and having a second substituent selected from (13) a $C_{1-4}$ alkyl group, (14) a $C_{3-7}$ cycloalkyl group, (15) an aryl group selected from phenyl or naphthyl or (16) an aralkyl group selected from benzyl or phenethyl, wherein the first and second substituents may be linked together with the nitrogen atom to form a cyclic amino group; wherein groups (b) and (c) may be substituted by 1 to 3 $C_{1-4}$ alkyl groups; and wherein groups (d) and (e) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino;

n is 1;

X is CH;

Y is a $C_{2-7}$ alkylene group;

$R^1$ is a hydroxy group, a $C_{1-4}$ alkoxy group, an aralkyloxy group selected from benzyloxy, phenethyloxy or naplithylmethyloxy, or an optionally substituted hydrocarbon group selected from:

(i) a $C_{1-8}$ aliphatic hydrocarbon group selected from an alkyl group, an alkenyl group or an alkynyl group;

(ii) a $C_{3-7}$ alicyclic hydrocarbon group selected from a cycloalkyl group or a cycloalkenyl group:

(iii) a $C_{4-9}$ alicyclic-aliphatic hydrocarbon group selected from a cycloalkyl-alkyl group or a cycloalkenyl-alkyl group;

(iv) a $C_{7-9}$ phenylalkyl, a $C_{11-13}$ naphthylalkyl or 2-phenylethenyl; or (v) an aromatic hydrocarbon group selected from phenyl or naphthyl;

wherein groups (ii) and (iii) may be substituted by 1 to 3 $C_{1-4}$ alkyl groups, and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino;

$R^2$ is a hydrogen atom, a halogen atom, a hydroxy group, a $C_{1-4}$ alkoxy group, an aralkyloxy group selected from benzyloxy, phenethyloxy or naphthylmethyloxy, or an optionally substituted hydrocarbon group selected from:

(i) a $C_{1-8}$ aliphatic hydrocarbon group selected from an alkyl group, an alkenyl group, or an alkynyl group;

(ii) a $C_{3-7}$ alicyclic hydrocarbon group selected from a cycloalkyl group or a cycloalkenyl group;

(iii) a $C_{4-9}$ alicyclic-aliphatic hydrocarbon group selected from a cycloalkylalkyl group or a cycloalkenyl-alkyl group;

(iv) a $C_{7-9}$ phenylalkyl, a $C_{11-13}$ naphthylalkyl or 2-phenylethenyl; or (v) an aromatic hydrocarbon group selected from phenyl or naphthyl;

wherein groups (ii) and (iii) may be substituted by 1 to 3 $C_{1-4}$ alkyl groups, and wherein groups (iv) and (v) may have 1 to 4 substituents selected from halogen, hydroxy, cyano, nitro, trifluoromethyl, $C_{1-4}$ alkoxy, $C_{1-4}$ alkyl, $C_{2-4}$ alkoxycarbonyl, $C_{1-3}$ alkylthio or $C_{1-4}$ alkylamino; and wherein either $R^1$ or $R^2$ and one carbon atom of Y may be linked together to form a ring; provided that

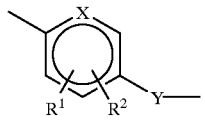

is other than

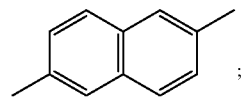

and L and M are each a hydrogen atom, or L and M are linked together to form a bond; or a pharmaceutically acceptable salt thereof and a pharmaceutically acceptable carrier.

5. The compound according to claim 1, wherein L and M are each a hydrogen atom; $R^2$ is a hydrogen atom; and the group R is attached through an alkylene group having 1 to 2 carbon atoms or an alkenylene group having two carbon atoms.

6. The compound according to claim 1, wherein L and M are each a hydrogen atom; $R^1$ is a hydroxy group, a lower alkoxy group or an aralkyloxy group selected from benzyloxy, phenethyloxy, or naphthylmethyloxy; $R^2$ is a hydrogen atom; and the group R is attached through an alkylene group having 1 to 2 carbon atoms or an alkenylene group having two carbon atoms.

7. The composition according to claim 4, wherein Y is —$CH_2CH_2$—.

8. The compound according to claim 1, wherein Y is —$CH_2CH_2$—.

9. The compound according to claim 1, wherein the hydrocarbon chain in the definition of R is —CH=CH— or —$CH_2CH_2$—, or a salt thereof.

10. The compound according to claim 1, wherein L and M are each a hydrogen atom, or a salt thereof.

11. The compound according to claim 1, wherein $R^2$ is a hydrogen atom, or a salt thereof.

12. The compound according to claim 1, which is 5-[3-[3-methoxy-4-(5-methyl-2-phenyl-4-oxazolylmethoxy) phenyl]-propyl]-2,4-thiazolidinedione, or a salt thereof.

* * * * *